US011646101B2

(12) United States Patent
Gao et al.

(10) Patent No.: US 11,646,101 B2
(45) Date of Patent: May 9, 2023

(54) CONTINUOUS WAVELET-BASED DYNAMIC TIME WARPING METHOD AND SYSTEM

(71) Applicant: KING ABDULLAH UNIVERSITY OF SCIENCE AND TECHNOLOGY, Thuwal (SA)

(72) Inventors: Xin Gao, Thuwal (SA); Renmin Han, Thuwal (SA); Sheng Wang, Thuwal (SA); Yu Li, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 1008 days.

(21) Appl. No.: 16/432,123

(22) Filed: Jun. 5, 2019

(65) Prior Publication Data
US 2020/0035325 A1    Jan. 30, 2020

Related U.S. Application Data

(60) Provisional application No. 62/702,653, filed on Jul. 24, 2018.

(51) Int. Cl.
    *G16B 30/00*    (2019.01)
(52) U.S. Cl.
    CPC .................... *G16B 30/00* (2019.02)
(58) Field of Classification Search
    CPC ........................................... G16B 30/00
    (Continued)

(56) References Cited

PUBLICATIONS

Chen Yang, Justin Chu, René L Warren, Inan Birol, NanoSim: nanopore sequence read simulator based on statistical characterization, GigaScience, vol. 6, Issue 4, Apr. 2017 (Year: 2017).*
(Continued)

*Primary Examiner* — G Steven Vanni
*Assistant Examiner* — Guozhen Liu
(74) *Attorney, Agent, or Firm* — Patent Portfolio Builders PLLC

(57) ABSTRACT

A method for global mapping between a first sequence $X_p$ and a second sequence $X_g$. The method includes receiving the first sequence $X_p$ and the second sequence $X_g$ at a computing device, wherein the first sequence $X_p$ is related to measured raw electrical current signals and the second sequence $X_g$ is related to calculated electrical current signals; applying a continuous wavelet transform (CWT) algorithm to each of the first and second sequences $X_p$ and $X_g$ to obtain raw CWT signals and expected CWT signals, respectively; extracting raw features and expected features from the raw CWT signals and the expected CWT signals, respectively; generating a context-dependent boundary $B_I$ around a previous warping path $W_I$, wherein the previous warping path $W_I$ is calculated using a dynamic time warping (DTW) algorithm that relates the raw features to the expected features and I is an index associated with an element of the previous warping path; calculating a new warping path $W_{I-1}$ based on the context-dependent boundary $B_I$; and identifying a nucleotide sequence associated with the first sequence $X_p$ and the second sequence $X_g$, based on the new warping path $W_{I-1}$.

20 Claims, 16 Drawing Sheets

(58) Field of Classification Search
USPC .......................................................... 702/20
See application file for complete search history.

(56) References Cited

PUBLICATIONS

Marcus Stoiber, Joshua Quick, Rob Egan et al.: "De novo Identification of DNA Modifications Enabled by Genome-Guided Nanopore Signal Processing", bioRxiv 094672; doi: https://doi.org/10.1101/094672. Posted Apr. 10, 2017 (Year: 2017).*

Yang Zhang and Thomas F. Edgar: "A Robust Dynamic Time Warping Algorithm for Batch Trajectory Synchronization", 2008 American Control Conference Westin Seattle Hotel, Seattle, Washington, USA, Jun. 11-13, 2008 (Year: 2008).*

Al-Naymat, G., et al., "SparseDTW: A Novel Approach to Speed up Dynamic Time Warping," in Proceedings of the Eighth Australasian Data Mining Conference, Dec. 1-4, 2009, vol. 101, pp. 117-127, Australian Computer Society, Inc.

Byrne, A. et al., "Nanopore Long-Read RNAseq Reveals Widespread Transcriptional Variation Among the Surface Receptors of Individual B Cells," Nature Communications, Jul. 19, 2017, Article No. 16027, pp. 1-11.

Chu, S., et al. "Iterative Deepening Dynamic Time Warping for Time Series," in Proceedings of the 2002 SIAM International Conference on Data Mining, Jan. 2002, pp. 195-212, SIAM.

David, M., et al., "Nanocall: An Open Source Basecaller for Oxford Nanopore Sequencing Data," Bioinformatics, Sep. 10, 2016, pp. 49-55.

Jain, M., et al., "Improved Data Analysis for the MinION Nanopore Sequencer," Nature Methods, Feb. 16, 2015, vol. 12, No. 4, pp. 351-356.

Keogh, E., et al., "Exact Indexing of Dynamic Time Warping," Knowledge and Information Systems, Mar. 1, 2015, vol. 7, No. 3, pp. 358-386.

Keogh, E.J., et al., "Scaling up Dynamic Time Warping for Datamining Applications," in Proceedings of the Sixth ACM SIGKDD International Conference on Knowledge discovery and data mining, Aug. 20-23, 2000, pp. 285-289, ACM.

Lemire, D., "Faster Retrieval with a Two-Pass Dynamic-Time-Warping Lower Bound," Pattern Recognition, Sep. 2009, vol. 42, No. 9, pp. 2169-2180.

Loose, M., et al., "Real-Time Selective Sequencing Using Nanopore Technology," Nature Methods, Sep. 2016, vol. 13, No. 9, pp. 751-754.

Lu, H., "Oxford Nanopore MinION Sequencing and Genome Assembly," Genomics Proteomics Bioinformatics, Sep. 17, 2016, vol. 14, No. 5, pp. 265-279.

Mallat, S.G., "A Theory for Multiresolution Signal Decomposition: The Wavelet Representation," IEEE Transactions an Pattern Analysis and Machine Intelligence, Jul. 1989, vol. 11, No. 7, pp. 674-693.

Metzker, M.L., "Sequencing Technologies—The Next Generation," Nature Reviews, Genetics, Jan. 1010, vol. 11, No. 1, pp. 31-46.

Müller, M. et al., "An Efficient Multiscale Approach to Audio Synchronization," in Proceedings of the 6th International Conference on Music Information Retrieval, Oct. 2006, pp. 192-197.

Prätzlich, T., et al., "Memory-Restricted Multiscale Dynamic Time Warping," in Acoustics, Speech and Signal Processing (ICASSP), 2016 IEEE International Conference on, Mar. 1, 2016, pp. 569-573, IEEE.

Ratanamahatana, C.A., et al., "Three Myths about Dynamic Time Warping Data Mining," in Proceedings of the 2005 SIAM International Conference on Data Mining, Mar. 24, 2005, pp. 506-510.

Salvador, S. et al., "FastDTW: Toward Accurate Dynamic Time Warping in Linear Time and Space," Intelligent Data Analysis, Oct. 1, 2007, vol. 11, No. 5, pp. 561-580.

Silva, D.F., et al., "Speeding Up All-Pairwise Dynamic Time Warping Matrix Calculation," Proceedings of the 2016 SIAM International Conference on Data Mining, May 5-7, 2016, pp. 837-845.

Simpson, J.T, et al., "Detecting DNA Cytosine Methylation Using Nanopore Sequencing," Nature Methods, Apr. 2017, vol. 14, No. 4, pp. 407-410.

Song, J.Z., et al., "The Wavelet-Based Cluster Analysis for Temporal Gene Expression Data," EURASIP Journal on Bioinformatics and Systems Biology, Jan. 1, 2017, vol. 2007, pp. 1-7.

Stoiber, M., et al., "BasecRAWller: Streaming Nanopore Basecalling Directly from Raw Signal," bioRxiv, May 1, 2017, p. 1-15.

Szalay, T., et al., "De Novo Sequencing and Variant Calling with Nanopores Using PoreSeq.," Nature Biotechnology, Letters, Oct. 2015, vol. 33, No. 10, pp. 1087-1091.

Torrence, C., et al., "A Practical Guide to Wavelet Analysis," Bulletin of the American Meteorological Society, Jan. 1998, vol. 79, No. 1, pp. 61-78.

\* cited by examiner

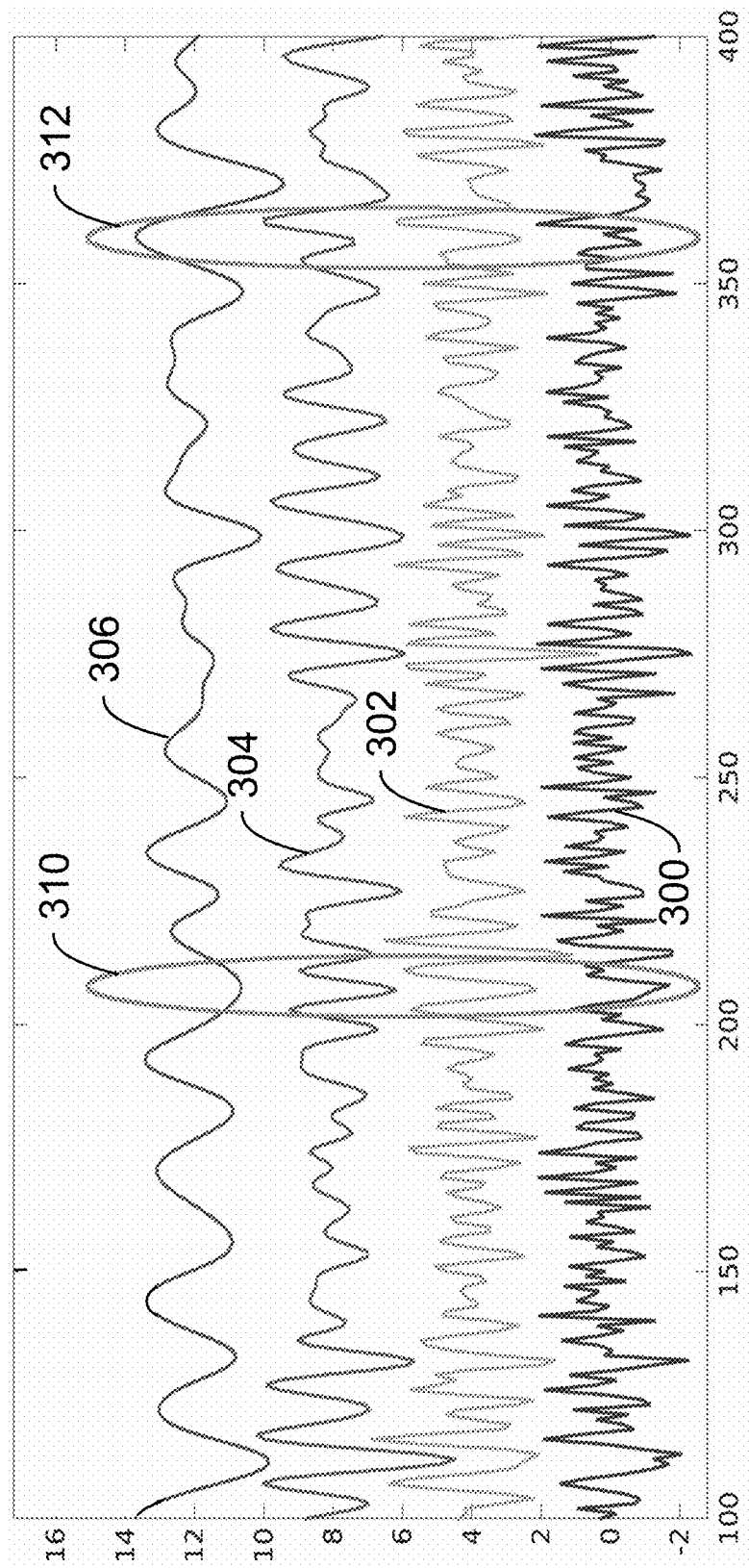

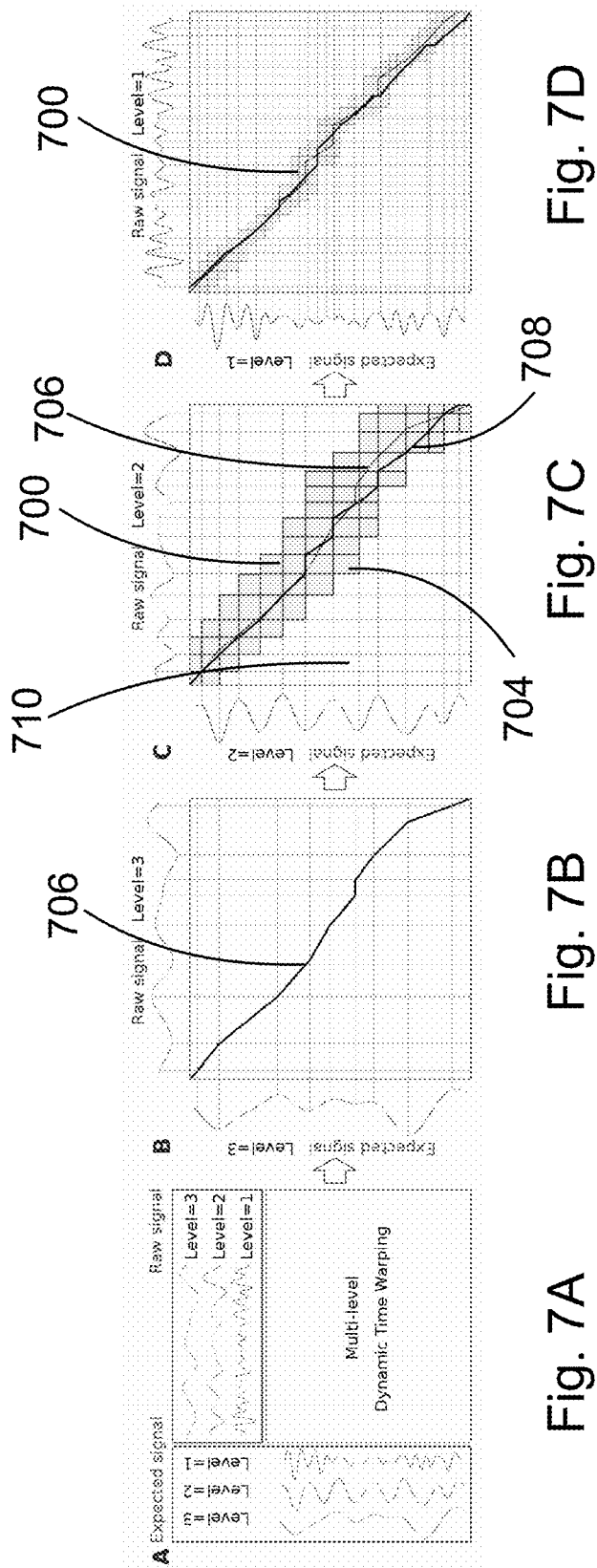

Algorithm 1: cwDTW

Input: $X_p, X_g, L, r, s_0$

1 Procedure cwDTW($X_p, X_g, L, r, s_0$)
2     Initialization: $l \leftarrow L, \alpha = |X_p|/|X_g|$ ;
3     while $l \geq 1$ do
4         $X_p^l = \text{CWT}(X_p, \alpha \cdot 2^{l-1} s_0)$ ;
5         $[I_{X_p^l}, P_{X_p^l}] = \text{PickPeaks}(X_p^l)$ ;
6         $X_g^l = \text{CWT}(X_g, 2^{l-1} s_0)$ ;
7         $[I_{X_g^l}, P_{X_g^l}] = \text{PickPeaks}(X_g^l)$ ;
8         if $l = L$ then
9             $W_{l=L} = \text{DTW}(P_{X_g^L}, P_{X_p^L})$;
10         else
11             $B_l = \text{ReMapIndex}(W_{l+1}, r)$ ;
12             $W_l = \text{cDTW}(P_{X_g^l}, P_{X_p^l}, B_l)$;
13         end
14         $l \leftarrow l - 1$;
15     end
16     Return $W_{l=0} = \text{cDTW}(P_{X_g}, P_{X_p}, B_{l=1})$;

Fig. 8

Table 1

| | Radius | 10 | 20 | 30 | 40 | 50 | 60 | 70 | 80 | 90 | 100 |
|---|---|---|---|---|---|---|---|---|---|---|---|
| HM4530 | FastDTW | 323% | 311% | 295% | 277% | 261% | 253% | 244% | 228% | 218% | 208% |
| | cwDTW (2) | 16.8% | 4.8% | 2.1% | 1.1% | 0.6% | 0.4% | 0.3% | 0.2% | 0.2% | 0.2% |
| | cwDTW ($\sqrt{2}$) | 11.5% | 2.6% | 1.1% | 0.6% | 0.4% | 0.3% | 0.2% | 0.2% | 0.2% | 0.1% |
| | cwDTW (1) | 10.6% | 2.3% | 0.9% | 0.5% | 0.3% | 0.2% | 0.2% | 0.2% | 0.1% | 0.1% |
| PP4782 | FastDTW | 473% | 458% | 431% | 416% | 401% | 395% | 386% | 373% | 365% | 359% |
| | cwDTW (2) | 30.6% | 9.4% | 3.7% | 1.7% | 0.9% | 0.6% | 0.4% | 0.3% | 0.2% | 0.1% |
| | cwDTW ($\sqrt{2}$) | 22.2% | 4.8% | 1.3% | 0.5% | 0.2% | 0.1% | 0.1% | 0.1% | 0.0% | 0.0% |
| | cwDTW (1) | 19.1% | 3.8% | 1.0% | 0.4% | 0.2% | 0.1% | 0.1% | 0.0% | 0.0% | 0.0% |

Fig. 11

Table 2

| | | 10 | 20 | 30 | 40 | 50 | 60 | 70 | 80 | 90 | 100 |
|---|---|---|---|---|---|---|---|---|---|---|---|
| PP4782F | FastDTW | 107% | 75% | 59% | 49% | 43% | 38% | 34% | 32% | 29% | 28% |
| | cwDTW (2) | 19.3% | 8.7% | 4.5% | 2.5% | 1.5% | 0.9% | 0.6% | 0.4% | 0.3% | 0.2% |
| | cwDTW ($\sqrt{2}$) | 17.1% | 6.8% | 2.8% | 1.4% | 0.7% | 0.4% | 0.2% | 0.1% | 0.1% | 0.1% |
| | cwDTW (1) | 15.7% | 5.7% | 2.3% | 0.9% | 0.4% | 0.2% | 0.1% | 0.1% | 0.0% | 0.0% |
| HM4530F | FastDTW | 89% | 61% | 47% | 38% | 33% | 28% | 25% | 23% | 21% | 20% |
| | cwDTW(2) | 14.6% | 6.8% | 3.8% | 2.4% | 1.5% | 1.0% | 0.7% | 0.5% | 0.3% | 0.2% |
| | cwDTW($\sqrt{2}$) | 13.7% | 6.2% | 3.1% | 1.6% | 0.9% | 0.5% | 0.3% | 0.2% | 0.1% | 0.1% |
| | cwDTW(1) | 13.1% | 5.8% | 2.6% | 1.1% | 0.5% | 0.3% | 0.1% | 0.1% | 0.0% | 0.0% |

Fig. 12

CONTINUOUS WAVELET-BASED DYNAMIC TIME WARPING METHOD AND SYSTEM

CROSS-REFERENCE TO RELATED APPLICATIONS

This application claims priority to U.S. Provisional Patent Application No. 62/702,653, filed on Jul. 24, 2018, entitled "CONTINUOUS WAVELET-BASED DYNAMIC TIME WARPING METHOD AND SYSTEM," the disclosure of which is incorporated herein by reference in its entirety.

BACKGROUND

Technical Field

Embodiments of the subject matter disclosed herein generally relate to a system and method for nanopore sequencing, and more specifically, to performing global mapping of two long signals with unbalanced scales for nanopore sequencing.

Discussion of the Background

DNA sequencing has been dominated by sequencing-by-synthesis technologies for decades [1]. Nowadays, single-molecule sequencing based on nanopore technologies has emerged with the promises of long-reads, point-of-care, and PCR-free [2]. Long-reads provides great potentials for de novo transcriptome analysis, which is able to span more repetitive regions and multiple exon junctions [3]; point-of-care makes it possible for the sequencing to be conducted immediately at anywhere in real-time [4]; and PCR-free allows the direct identification of epigenetics [5].

The innovation brought by the nanopore sequencing is the direct measurement of the changes in the electrical current signal 102 (also called the raw signal) when a single-strand DNA 110 passes through a nanopore 112 of a membrane 114 [6], as illustrated in FIG. 1. The system 100 of FIG. 1 shows that a power source 120 biases the membrane 114 with a given voltage to force the single-strand DNA 110 to pass through the nanopore. During this process, the changes in voltages due to the DNA are measured by a measurement device 122 and they represent the electrical current signal 102. An expected current signal due to the passing of the single-strand DNA 112 through the nanopore is shown as element 130. The expected current signal 130 is calculated based on a pore model and the corresponding nucleotide sequence 132 corresponding to the expected current signal 130 is then identified with, for example, a basecalling module.

Without the needs for polymerase chain reaction (PCR) amplification, nanopore sequencing generates extremely long reads, typically ranging from 12 k to 120 k bp. At each time point, there are k consecutive nucleotides in a pore (denoted as a k-mer, where k is often 5 or 6). The electrical current signal is measured for each time point of the pore. The pore model describes the expected electrical current values 130 for different k-mers. In nanopore sequencing, the frequency of the electrical current measurements and the speed of the DNA sequence passing through the pore are not coordinated, which causes the main technical difficulty for nanopore data analysis. In practice, the frequency of the electrical current measurements is 7-9 times higher than the passing speed of the DNA sequence, resulting in an order of magnitude difference in the sampling rates of the raw signal sequence 102 and the expected signal sequence 130 from the pore model.

Among various steps in nanopore data analysis, the global mapping between the raw electrical current signal sequence 102 and the expected signal sequence 130 from the pore model serves as the key to base calling [7], variant identification [8], and methylation detection [5] (see element 140 in FIG. 1). Dynamic time warping (DTW) is the most widely-used technique that finds an optimal mapping between two temporal sequences that vary in speed. In DTW, the sequences are warped non-linearly by stretching or shrinking along the time axis [9]. The original DTW has an $O(L_1*L_2)$ time complexity, where $L_1$ and $L_2$ are the lengths of the two sequences to be mapped. This complexity severely limits DTW's applications in various problems that have long sequences, such as nanopore sequencing. To accelerate the analysis of long sequences, a variety of improved DTW have been proposed, which can be roughly categorized into three classes: constrained DTW, coarsening DTW, and multi-level DTW.

Constrained DTW (e.g., SparseDTW [10] and PrunedDTW [11]), whose accuracy lies on the strategy of bounding, casts an arbitrary or a specific boundary to reduce the search space [12]. Coarsening DTW (e.g., Multi-scaleDTW [13, 14]) speeds up DTW by operating on a reduced representation of the signals, which is often produced by down-sampling or equal averaging, and then projecting the low-resolution warping path to the full resolution [15, 16]. Yet, the calculated final warping path becomes increasingly inaccurate as the level of coarsening increases. Multi-level DTW (e.g., FastDTW [9]) combines the ideas of constrained and coarsening DTW. It recursively projects a solution from a low-resolution representation generated by coarsening DTW and refines the projected warping path in high-solution via constrained DTW.

Nevertheless, all aforementioned variants of DTW have high risks of failure when the input sequences are noisy and have unbalanced sampling rates, and none of the existing DTW variants can achieve a good balance between accuracy and efficiency on mapping extremely long sequences with unbalanced scales.

Thus, there is a need for a new method that is capable to avoid the above noted problems.

SUMMARY

According to an embodiment, there is a method for global mapping between a first sequence $X_p$ and a second sequence $X_g$. The method includes receiving the first sequence $X_p$ and the second sequence $X_g$ at a computing device, wherein the first sequence $X_p$ is related to measured raw electrical current signals and the second sequence $X_g$ is related to calculated electrical current signals; applying a continuous wavelet transform (CWT) algorithm to each of the first and second sequences $X_p$ and $X_g$ to obtain raw CWT signals and expected CWT signals, respectively; extracting (1304) raw features and expected features from the raw CWT signals and the expected CWT signals, respectively; generating a context-dependent boundary $B_I$ around a previous warping path $W_I$, wherein the previous warping path $W_I$ is calculated using a dynamic time warping (DTW) algorithm that relates the raw features to the expected features and I is an index associated with an element of the previous warping path; calculating a new warping path $W_{I-1}$ based on the context-dependent boundary $B_I$; and identifying a nucleotide sequence associated with the first sequence $X_p$ and the second sequence $X_g$, based on the new warping path $W_{I-1}$.

According to another embodiment, there is a computing device for global mapping between a first sequence $X_p$ and a second sequence $X_g$. The computing device includes an interface configured to receive the first sequence $X_p$ and the second sequence $X_g$, wherein the first sequence $X_p$ is related to measured raw electrical current signals and the second sequence $X_g$ is related to calculated electrical current signals and a processor connected to the interface. The processor is configured to apply a continuous wavelet transform (CWT) algorithm to each of the first and second sequences $X_p$ and $X_g$ to obtain raw CWT signals and expected CWT signals, respectively, extract raw features (322B) and expected features from the raw CWT signals and the expected CWT signals, respectively, generate a context-dependent boundary $B_I$ around a previous warping path $W_I$, wherein the previous warping path $W_I$ is calculated using a dynamic time warping (DTW) algorithm that relates the raw features to the expected features and I is an index associated with an element of the previous warping path, calculate a new warping path $W_{I-1}$ based on the context-dependent boundary $B_I$, and identify a nucleotide sequence associated with the first sequence $X_p$ and the second sequence $X_g$, based on the new warping path $W_{I-1}$.

According to still another embodiment, there is a non-transitory computer readable medium including computer executable instructions, wherein the instructions, when executed by a processor, implement instructions for executing the steps noted above.

BRIEF DESCRIPTION OF THE DRAWINGS

The accompanying drawings, which are incorporated in and constitute a part of the specification, illustrate one or more embodiments and, together with the description, explain these embodiments. In the drawings:

FIG. 3A illustrates a first sequence and its continuous wavelet transforms with different scales and FIG. 3B illustrates a second, different, sequence and its continuous wavelet transforms with different scales;

FIGS. 7A to 7D schematically illustrate how the constrained DTW algorithm works;

FIG. 8 shows a software implementation of the cwDTW algorithm;

FIG. 11 illustrates the improved accuracy of the cwDTW algorithm in recognizing exiting complex genomes comparative with other methods and the influence of various parameters of the algorithm;

FIG. 12 illustrates the improved accuracy of the cwDTW algorithm in recognizing exiting simple genomes comparative with other methods and the influence of various parameters of the algorithm;

DETAILED DESCRIPTION

Figure 1:
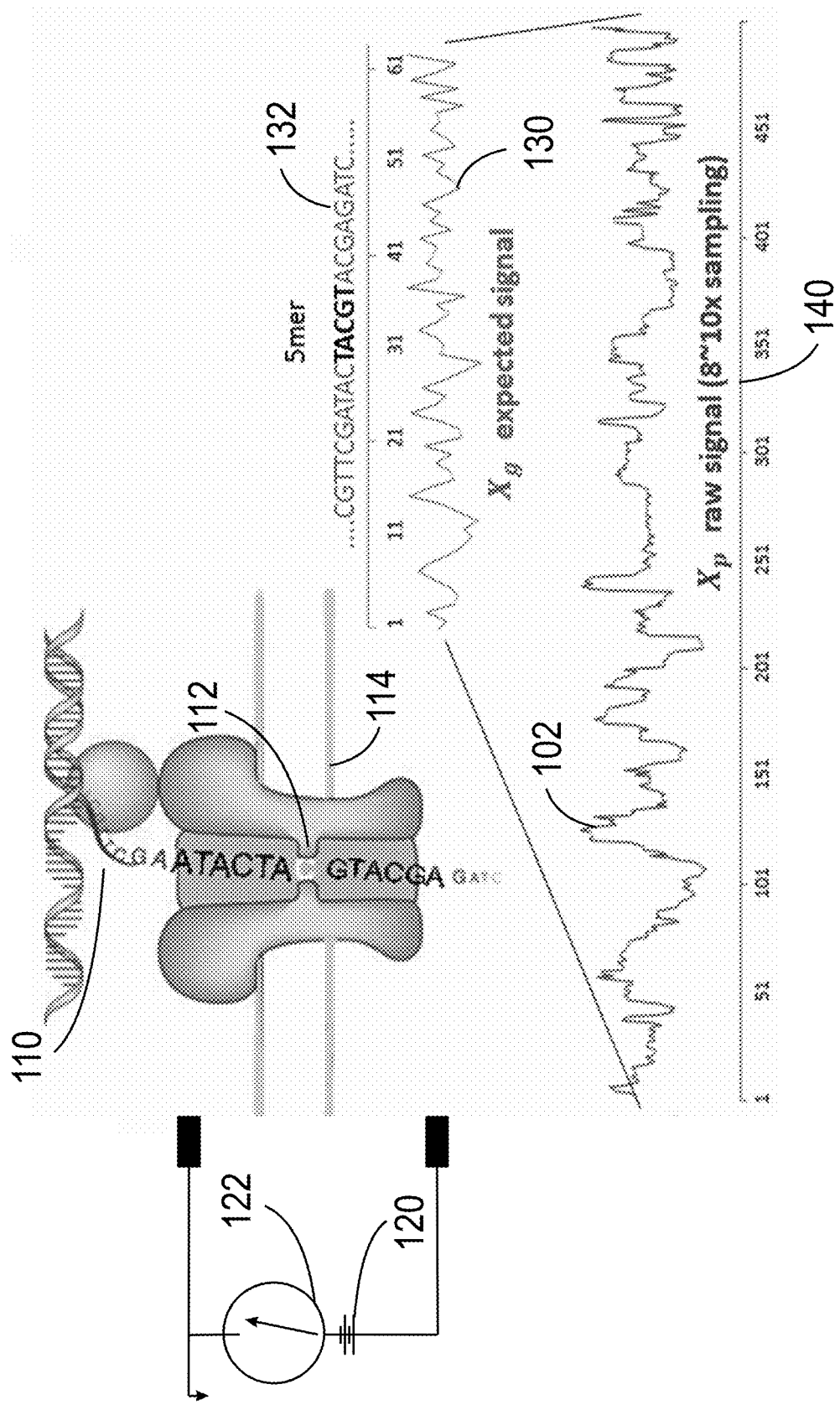
FIG. 1 is a schematic illustration of a Nanopore sequencing device.

The following description of the embodiments refers to the accompanying drawings. The same reference numbers in different drawings identify the same or similar elements. The following detailed description does not limit the invention. Instead, the scope of the invention is defined by the appended claims.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, a continuous wavelet-based DTW (cwDTW) method is introduced, which is an improved multi-level Dynamic Time Warping (DTW) framework based on Continuous Wavelet Transform (CWT). According to an aspect of the cwDTW method, it is desired to obtain a series of highly representative coarsening signals at different resolution levels via CWT on input signals in consideration of their unbalanced temporal ratio. Thus, at each resolution level, the transformed coarsening signals from the two inputs would reside in comparable length and similar shape. Followed the multi-level DTW framework, a context-dependent boundary enables a stable and narrow search space in each level, which allows this embodiment to achieve the global mapping of two lengthy signals with unbalanced scales in linear time and space.

In one application, the cwDTW method benefits from the continuous scale analysis succeeded from CWT and is able to utilize the highly representative information embedded in input signals. The cwDTW algorithm has an approximate O(N) time- and space-complexity, where N is the length of the longer sequence, and substantially advances previous methods in terms of the mapping accuracy. Comprehensive experimental results obtained by the inventors demonstrated the efficiency and effectiveness of the cwDTW method. Furthermore, the cwDTW method is not only able to align the raw and expected signal sequences in nanopore, but is also applicable to other temporal sequence mapping problems based on biological, video, audio and graphical data.

Long-reads, point-of-care, and PCR-free are the three promises brought by nanopore sequencing, in which the raw signal measured by nanopore provides essential information for downstream analysis such as base-calling and epigenetic detection. The cwDTW method, which aims to perform globally mapping two long signals with unbalanced scales, is suitable for nanopore sequencing analysis since the raw signal is about 8-10 times longer than the genomic translated signal.

Before discussing the details of the cwDTW method, a brief introduction to the continuous wavelet transform and dynamic time warping is believed to be in order.

The continuous wavelet transform (CWT) is used to divide a continuous-time function into wavelets. In particular, the CWT of a one-dimensional signal X(t) at a scale $a \varepsilon \mathbb{R}^2$ and translational value $b \in \mathbb{R}$, is denoted as $X_{a,b}$ and is expressed by the following integral:

$$X_{a,b} = \frac{1}{\sqrt{a}} \int_{-\infty}^{\infty} X(t)\psi_{a,b}(t)dt, \text{ where } \psi_{a,b}(t) = \psi\left(\frac{t-b}{a}\right) \quad (1)$$

is the mother wavelet which is a continuous function in both the time domain and the frequency domain. In this implementation of the cwDWT method, the Mexican hat wavelet $\psi(t)=(1-t^2)\exp^{-2/2}$ is selected to be the wavelet function, but other wavelet functions may be used [18].

The other ingredient for the novel cwDWT method, is the DWT algorithm. The DTW for mapping two input signal sequences is as follows: given two input signal sequences $X=x_1, x_2, \ldots, x_{L1}$ and $Y=y_1, y_2, \ldots, y_{L2}$ of lengths $L_1$ and $L_2$ respectively, construct a warping path $W=w_1, w_2, \ldots, w_L$ to minimize the distance measurement $\text{Dist}(W)=\Sigma_l^{L=1L} c(w_{li}, w_{lj})$, where L is the length of the warping path and $c(w_{li}, w_{lj})$ is the Euclidean distance of the $l^{th}$ aligned element between the two signal points $x_i$ and $y_j$. To determine the optimal path W, an $(L_1 \times L_2)$ matrix D is recursively computed, in which the matrix entry D(n, m) is the total cost of an optimal path between X and Y. For the original DTW algorithm, the $D(i,j)=\min\{D(i-1,j-1), D(i,j-1), D(i-1,j)\}+c(i,j)$ and c is the distance between element $x_i$ in X and $y_j$ in Y. D(n, m) can be exactly solved by dynamic programming, resulting in the globally optimal mapping. However, note that this original DTW algorithm does not uses a content-dependent boundary to limit the calculations of the D(i,j) elements. As will be discussed later, the cwDTW method generates such content-dependent boundary for each scale of the CWT signals, and iteratively calculates the optimal mapping between the two input sequences X and Y, as the scale becomes finer and finer.

Though DTW has been well-established, the original DTW has $O(L_1L_2)$ time complexity and needs a matrix D with $L_1 \times L_2$ dimension, which is too inefficient and memory-costly for any computing device for extremely long sequences, such as the ones from nanopore sequencing. To apply DTW in challenging applications, various versions of improved DTW have been proposed, such as FastDTW [9], SparseDTW [10], PrunedDTW [11], and MultiscaleDTW [13, 14].

Figure 2:
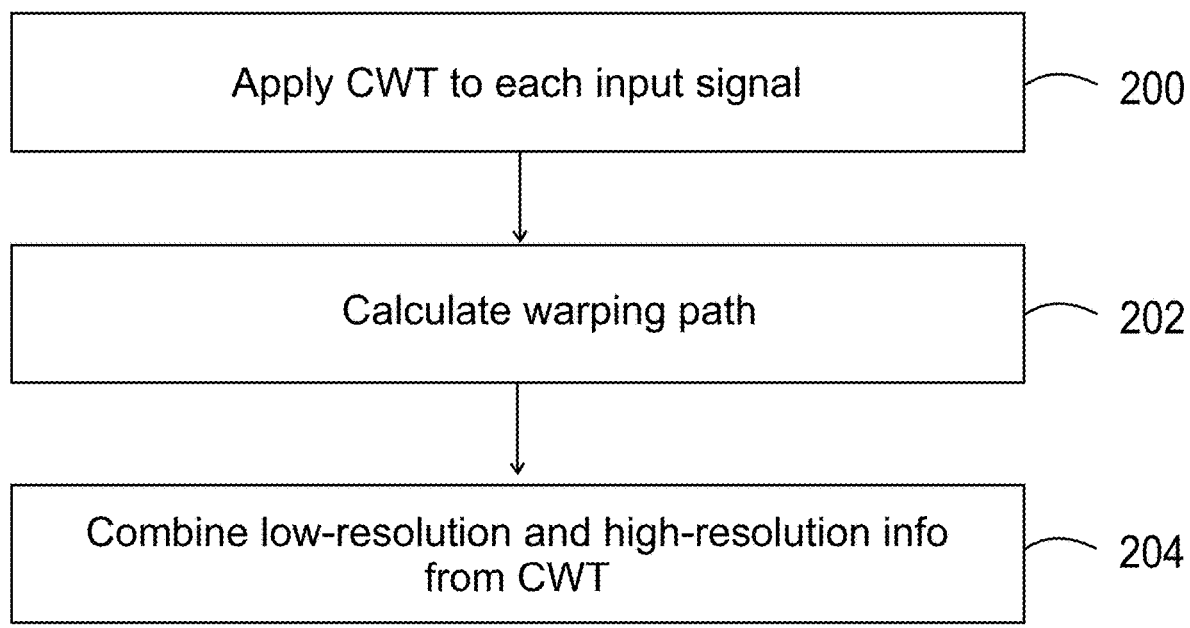
FIG. 2 is a flowchart of a method for calculating a global mapping between two different sequences.

The CWT and DTW methods are now integrated into the new cwDTW method for handling two sequences having different sizes. The DTW is further modified to be a context-dependent constrained DTW. Another ingredient that is added to the cwDTW method is the multi-level refinement. Briefly, the cwDTW method, a flowchart of which is illustrated in FIG. 2, includes the following steps: a step 200 in which a CWT representation is run on each input signal to obtain an informative representation, followed by peak and nadir picking to produce low-resolution signals with reduced lengths, a step 202 in which a context-dependent constrained DTW takes a warping path calculated at a lower resolution and determines what regions it passes through in a higher resolution; and a step 204 in which multi-level refinement combines the low-resolution and high-resolution information from CWT with different scales, and gradually refines the warping path where the level becomes finer and finer, until the final warping path at the original resolution of the input sequences is obtained.

Each step of this method is now discussed in more detail. With regard to step 200, both the raw signal 102 and the expected signal 130 need to be CWT transformed. When handling long signal sequences (as the raw signal and the expected signal), down sampling combined with multi-scale analysis is widely used by others to decrease the complexity of the signal sequences [9, 13, 14]. Compared with down sampling, wavelet representation is naturally more proper for multi-scale analysis [21], where both discrete wavelet transform and continuous wavelet transform can be used. Although there have been studies that combine discrete wavelet transform with dynamic time warping [22, 23, 24], such methods have clear limitations.

Discrete wavelet transform is an orthogonal wavelet analysis, in which the number of convolutions at each scale is proportional to the width of the wavelet basis at that scale. To apply discrete wavelet, an alignment to the power of 2 is necessary [23], which usually requires the padding of the signal. This produces a wavelet spectrum that contains discrete "blocks" of wavelet power and is useful for signal processing as it gives the most compact representation of the signal.

However, for temporal data analysis, an aperiodic shift in the time series produces a different wavelet spectrum. On the contrary, a nonorthogonal transform, such as CWT, is highly redundant at large scales, where the wavelet spectra at adjacent scales are highly correlated. CWT is thus more useful for time series analysis, where smooth and continuous wavelet transforms are expected. For this reason, the CWT is applied to both signal sequences 102 and 130. One aspect of applying the CWT to these signals is obtaining a feature representation of the CWT spectra.

In this regard, returning to equation (1), the transformed wavelet spectrum $X_{a,b}$ reflects the pattern matching between the input signal X and the wavelet function $\psi$. By changing the scale parameter a, larger values correspond to lower frequency signals whereas smaller values correspond to higher frequency signals. FIG. 3A shows the CWT spectra of an expected signal sequence $X_g$ 300 with different values of the scale parameter a. The expected signal sequence 300 is obtained by applying sliding windows of k-mers (here k=5) on the DNA sequence and using the expected electrical current value for each k-mer according to the pore model.

For convenience of analysis, this embodiment fixes the translational value b as the same index correspondence as X. That is, the transformed signals (spectrum) have the same length and retain peer-to-peer index to X. This embodiment uses CWT(X, a) to denote the transformed spectrum of X with the scale parameter a. In FIG. 3A, the input is an expected signal sequence 300 with the index from 100 to 400, and CWT with scales a as $\sqrt{2}$, $2\sqrt{2}$ and $4\sqrt{2}$ are applied, respectively (see spectra 302, 304, and 306, respectively). Although the details are blurred in the wavelet transformed signals, most peaks and nadirs in CWT(Xg, ·) maintain stability and retain their corresponding locations as in the original signals (e.g., regions 310 and 312). Furthermore, the shape of the CWT spectrum changes smoothly from a smaller scale value (see curve 302) to a larger one (see curve 306), which ensures the success of feature mapping from low-resolution representations to high-resolution ones, when using a multi-level algorithm. Note that curve 302 corresponds to CWT(X, $\sqrt{2}$), curve 304 corresponds to CWT(X, $2\sqrt{2}$) and curve 306 corresponds to CWT(X, $4\sqrt{2}$).

Figure 3B:
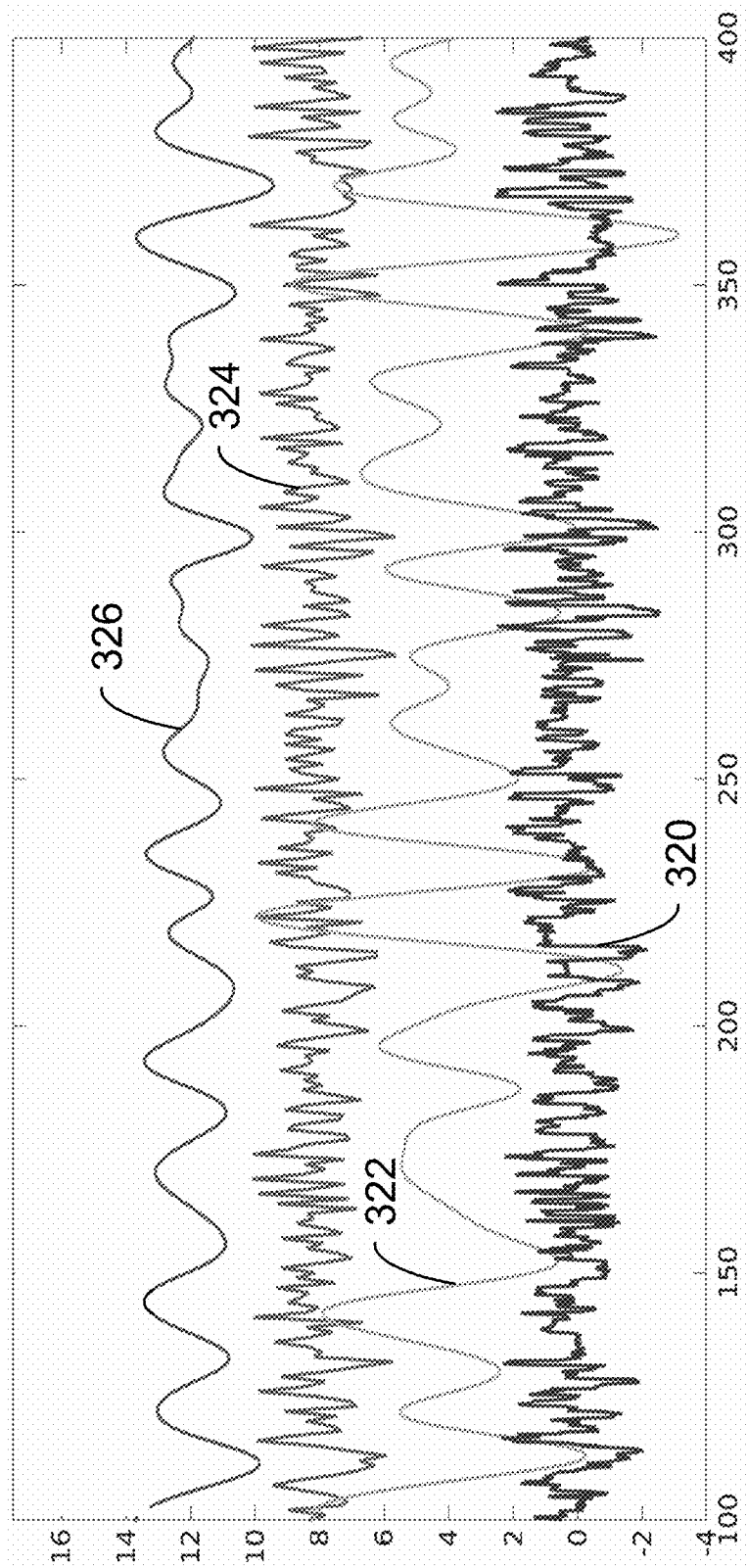

Next, a spectrum analysis of the two sequences based on CWT is discussed. FIG. 3B shows the CWT spectrum comparison of the expected signal sequence ($X_g$) 130 and the corresponding raw electrical current signal sequence ($X_p$) 102. Note that FIG. 3B shows the raw signal 102 as curve 320 and the expected signal 130 as curve 324. Further, FIG. 3B shows the CWT of the raw signal as curve 322 (raw CWT signal) and the CWT of the expected signal 130 as curve 326 (expected CWT signal). Because the lengths of the two signal sequences are one order of magnitude different, where $X_g$ ranges from 100 to 400 and the corresponding $X_p$ ranges from 800 to 3200, according to this embodiment, the index of $X_p$ is rescaled by ⅛ for the sake of visualization. That is, an additional scale $\alpha=8$ is applied to the CWT of $X_p$. It can be seen from FIG. 3B that the produced spectrum shape $CWT(X_p, 4\alpha\sqrt{2})$ 322 for the raw signal sequence 320 looks quite similar to that of $CWT(X_g, 4\sqrt{2})$ 326 for the expected signal sequence 324.

Figure 4:
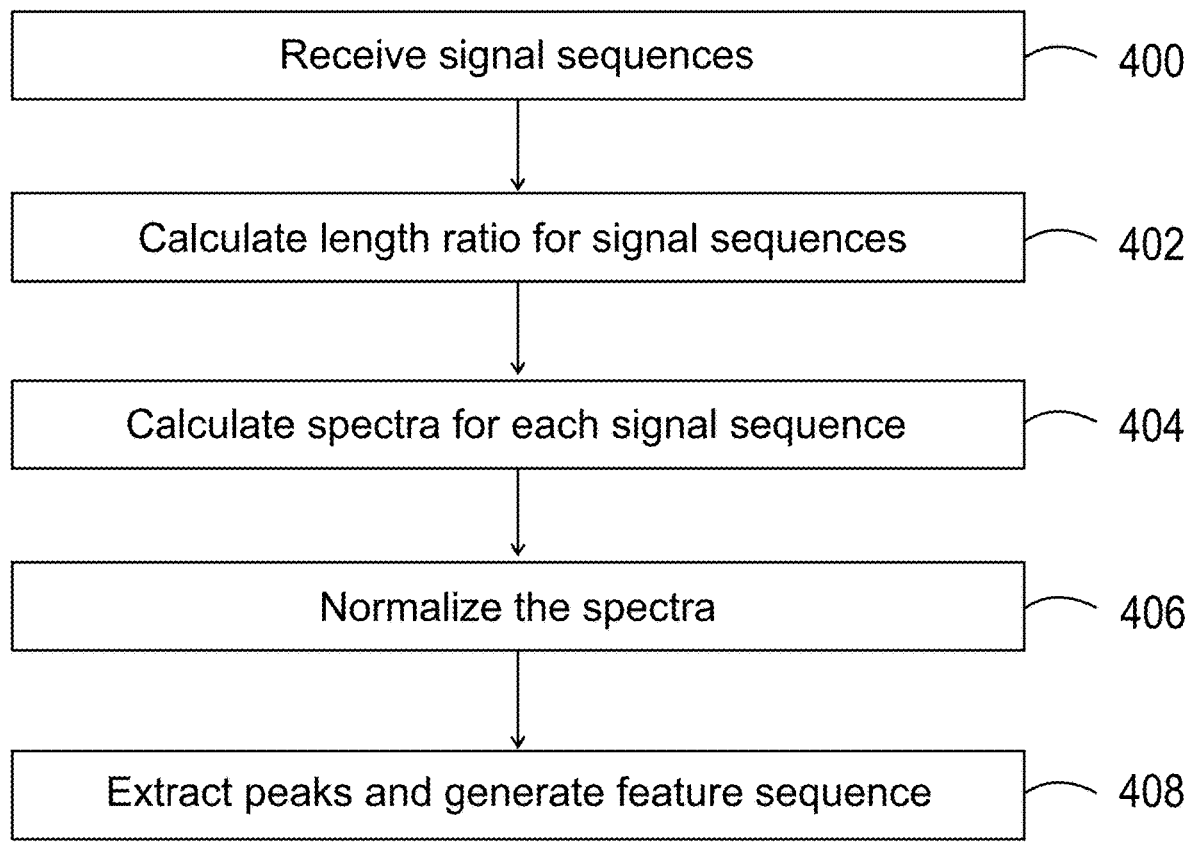
FIG. 4 is a flowchart of a method for extracting features from the first and second sequences.
Figure 5:
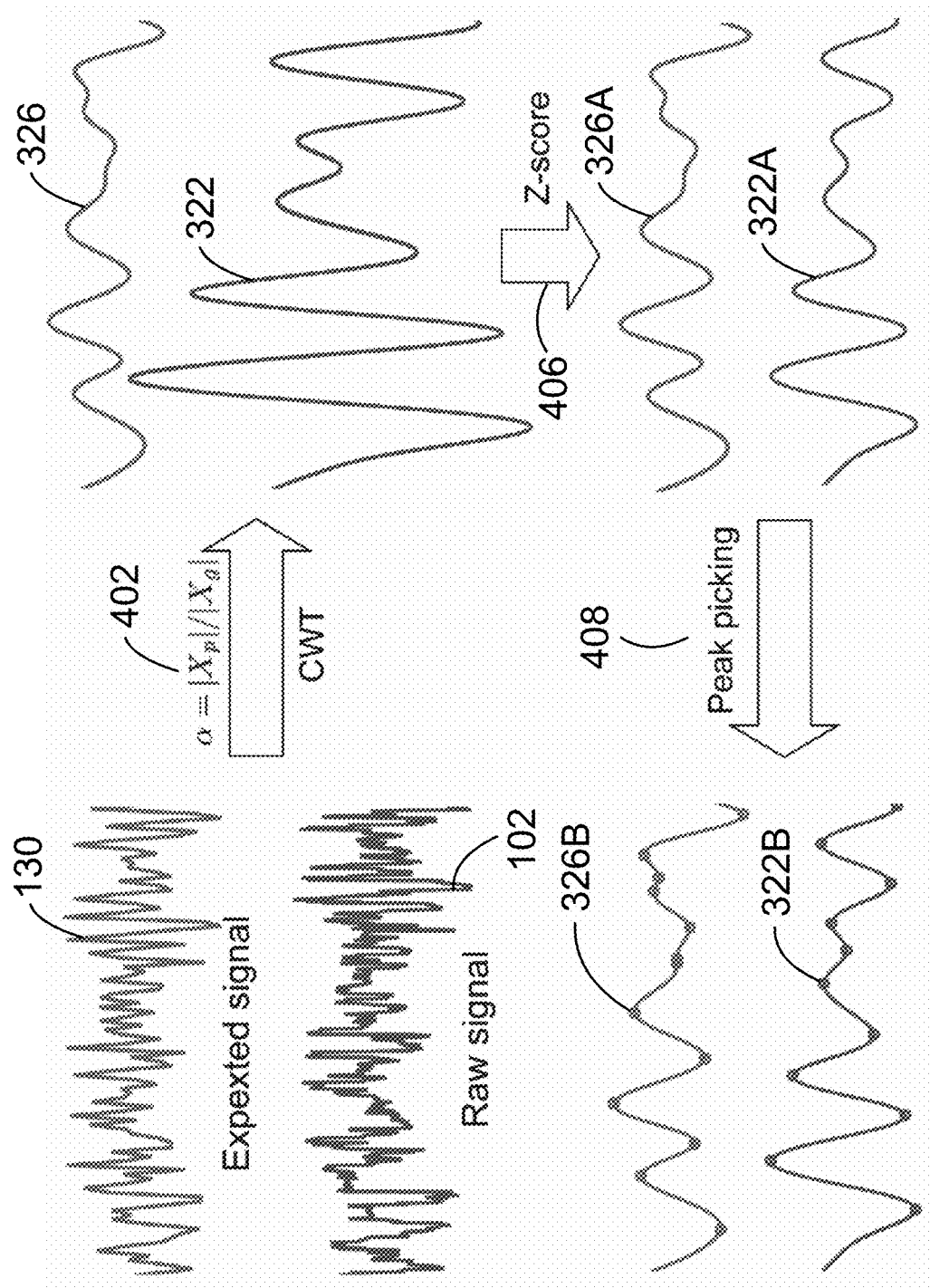
FIG. 5 schematically illustrates the process of extracting feature sequences from the first and second sequences.

According to this embodiment, the following feature extraction procedure, which copes with the unbalanced lengths of the raw signal sequence and the expected signal sequence, is implemented. As illustrated in FIG. 4, in step 400, the signal sequences Xg and Xp are received (see also FIG. 5). In step 402, a computing device calculates, for signal sequences Xg and Xp, the length ratio $\alpha=|Xp|/|Xg|$, where |X| returns the length of X. In step 404, the computing device obtains, for each scale a, the spectra CWT(Xg, a) 322 and CWT(Xp, α·a) 326, which is illustrated in FIG. 5. In step 406, the computing device calculates the Z-score and normalizes the spectra CWT(Xg, a) 322 and CWT(Xp, α·a) 326, based, for example, on the Z-score normalization. The normalized spectra are shown in FIG. 5 as curves 322A and 326A. Other normalization methods may be used. In step 408, the method extracts peaks and nadirs 322B and 326B from each spectrum (hereinafter, both the peaks and the nadirs are referred to as peaks) and these peaks are considered to be the feature sequence for each signal.

Note that the two input signal sequences 102 and 130 have unbalanced temporal scales due to the different sampling rates. After CWT spectra is calculated in step 404, in consideration of their unbalanced ratio and Z-score normalization, the input signals are converted to CWT spectra 322A and 326A with similar shapes. Then the feature sequences 322B and 326B are derived by peak picking to make their temporal scales comparable.

The peaks and nadirs of the CWT spectrum are extracted as features 322B and 326B and will be used for the consequent constrained dynamic time warping (the choice of features will be discussed in experiments). FIG. 5 illustrates one round of this procedure. Though the original signal sequences Xg and Xp have significantly different lengths, the numbers of the picked peaks and nadirs from CWT(Xg, a) 322 and CWT(Xp, α·a) 326 are quite similar.

Figure 6:
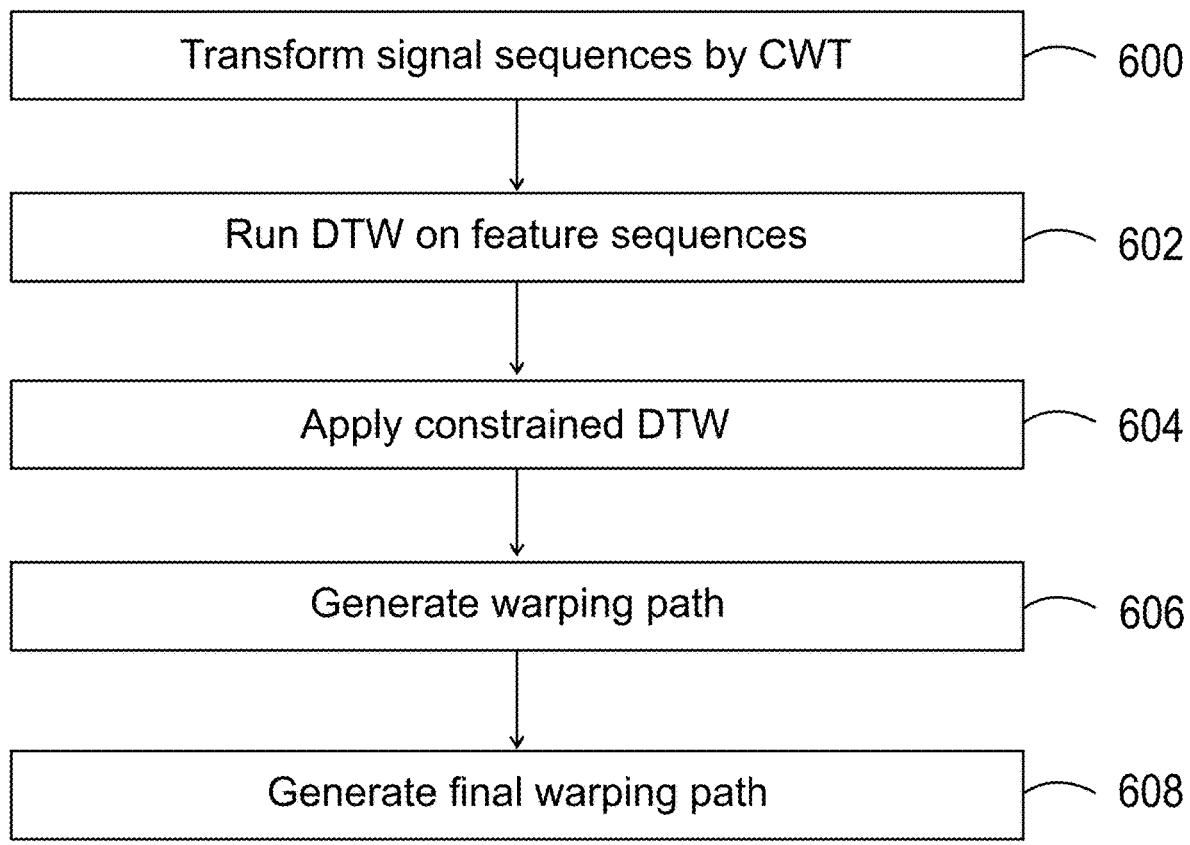
FIG. 6 is a flowchart of a method for applying a continuous wavelet DTW (cwDTW) algorithm to the first and second feature sequences.

Next, the context-dependent constrained DTW is discussed. The peaks 322B and 326B extracted from the CWT spectra 322 and 326 are considered as the spectrum features and are used in the multi-level dynamic time warping scheme. The goal in this embodiment is to gradually refine and generate finer warping paths when going from a coarser level to a finer one. The method starts in step 600 (see FIG. 6) from the coarsest level L, where the raw signal sequence 102 is transformed by CWT to $X_p^L=CWT(X_p, \alpha \cdot 2^{L-1}s_0)$ (corresponding to curve 322A in FIG. 5) and the expected signal sequence 130 is transformed to $X_g^L=CWT(X_g, 2^{L-1}s_0)$ (corresponding to curve 326A in FIG. 5 where $s_0$ is the base scale).

In step 602, the original DTW algorithm is run by dynamic programming on the feature sequences (i.e., peaks 322B and 326B) from these two transformed sequences 322A and 326A. To generate the warping path for the (L−1)th level, the method applies in step 604 the constrained DTW [12], where the constraints are not predefined, but rather determined by the warping path from the previous level L. That is, the warping paths for the (L−1)th level and the Lth level are not assumed to be the same. In fact, this step does not even assume that the two paths have any overlap at all. However, this step assumes that the warping path for the (L−1)th level is 'constrained' by the one for the Lth level. It should be noted that although the peaks for the (L−1)th level are much more than that for the Lth level, each peak in the (L−1)th level has a corresponding index interval in the Lth level. That is, there exists an index j, such that a given peak in the (L−1)th level resides between the indexes j and j+1 at the Lth level. This constraint thus requires that each element in the warping path of the (L−1)th level is assumed to be within the radius r distance from the corresponding element in the path of the Lth level, which makes the constraint to be context-dependent.

Given this context-dependent constraint, the constrained DTW is applied to generate in step 606 the warping path for the (L−1)th level, which is then used to form the context-dependent constraint for the (L−2)th level. This procedure is repeated until the raw signal level is reached, where the final warping path is generated in step 608.

Details about the context-dependent bounded DTW and the pseudo-code for the proposed context-bounded DTW are now discussed. It should be noticed that all the peaks in FIG. 5 are directly extracted from the CWT of the signals, which is the main difference between other multi-DTWs [9, 13, 14]. Different scales of CWT will result in peaks on different levels. In the present implementation, given the basescale $s_0$ and the level number L, for $l \leq L$, the l-th level scale is defined as $s_l=2^{l-1}s_0$. Consequently, the l-th CWT spectrum for the nanopore raw signal 102 and expected signal 130 are defined as $X_p^L=CWT(X_p, \alpha \cdot 2^{L-1}s_0)$ and $X_g^L=CWT(X_g, 2^{L-1}s_0)$, respectively.

The Peak extraction defined in step 408 is denoted as operation $[I_x^l, P_x^l]=PickPeaks(X^l)$, where $P_x^l$ is the peak value and $I_x^l$ is the peak indexed in sequence $X^l$. The algorithm starts with the most coarse level L. For $[I_{X_g^L}, P_{X_g^L}]=PickPeaks(X_g^L)$ and $[I_{X_p^L}, P_{X_p^L}]=PickPeaks(X_p^L)$, there are no reference or anchor points that can be used in the sequence mapping. Therefore, a primary DTW is used to map $P_{X_g^L}$ and $P_{X_p^L}$. Here, the generalized path from the Lth feature sequence is denoted as: $W_L=DTW(P_{X_g^L}, P_{X_p^L})$. For each $W_L=(i,j)$ element in $W_L$, a mapping related to $X_g$ and $Y_g$ can be obtained by remapping $I_{X_g^L}$ and $I_{X_p^L}$. For the (L−1)th level CWT spectrum $H_g^{(L-1)}$ and $X_p^{g_{L-1}}$, it is possible to constrain the search path with the obtained $W_L$ path. Generally, for an arbitrary lth level CWT spectra $X_g^l$ and $X_p^l$, their feature sequence $[I_{X_g^l}, P_{X_g^l}]=PickPeaks(X_g^l)$ and $[I_{X_p^l}, P_{X_p^l}]=PickPeaks(X_p^l)$, the method can accelerate the dynamic time warping of $P_{X_g^L}$ and $P_{X_p^L}$ based on $W_{l+1}$ as follows:

1. Given $W_{l+1}$, remap each $w_{l+1}=(i,j)$ to $X_g$ and $X_p$ to gain a global mapping $W_{l+1}^g$;
2. For each $w_{l+1}^g=(i^g, j^g)$, search in $I_{X_g^l}$ to find index sequence M(m ε M) with $I_{X_g^l}(m-1) \leq i^g$ and $I_{X_g^l}(m) \geq i^g$;
3. For each $w_{l+1}^g=(i^g, j^g)$, search in $I_{X_p^l}$ to find index sequence N(n ε N) with $I_{X_p^l}(n-1) \leq i^g$ and $I_{X_p^l}(n) \geq i^g$;
4. Make $\tilde{w}_l=(m, n)$, $\tilde{w}_l \varepsilon \tilde{W}_l$ as the anchor point between sequence $P_{X_g^l}$ and $P_{X_p^l}$;
5. Interpolate all the (m−1, n−1) and (m,n), i.e., fill the index gap in $\tilde{W}_l$ to create a warp path $W_l^*$; and
6. Generate search boundary from $W_l^*$ by extending every element (i,j) in four directions with r to create an area defined by i−r, i+r, j−r, j+r.

In doing so, with the I-th level CWT spectrum and the already known (I+1)-th path, a boundary area that encompasses the I-th path can be generated with a suitable search radius r. Here, the path remapping described above is $B_I=\text{ReMapIndex}(W_{I+1}^*, r)$, where $B_I$ is the boundary generated by $W_I^*$ with r searching radius. The cDWT can be applied to find the optimal warp path $W_I$ within the boundary area $B_I$. The following notation cDTW $(P_{X_g}^L, P_{X_p}^L, B_I)$ is used to denote the operation noted above.

FIGS. 7A to 7D show one example of the context-dependent constrained DTW with CWT level L=3 and radius r=1. It can be seen in FIG. 7C that the bounded constraint 700 for each finer level is determined by the warping path 706 from the coarser level, which not only significantly reduces the search space 704 from the original space 710, but also avoids an incorrect mapping at a coarser level being retained at finer levels. These features differentiate the present algorithm from other approximate DTW algorithms, which assume predefined constraints to reduce the search space. Although the present algorithm does not require the warping paths at two consecutive levels to overlap, they often do overlap in practice. This is due to the high correlation among the CWT spectra with different scales, which inherit the context of the raw signal sequence. Note that FIGS. 7C and 7D indicate the warping path of the coarser level by a dotted line 706 and the refined path at the finer level by a solid line 708.

The proposed cwDTW algorithm may be implemented as computer instructions as illustrated in FIG. 8 by Algorithm 1, where $X_p$ is the raw signal sequence 102 and $X_g$ is the expected signal sequence 130, L is the user-defined level, r is the searching radius, and so is the CWT base scale. CWT(·) is the continuous wavelet transform defined above, PickPeaks(·) is the peak picking procedure described above with regard to FIGS. 3A and 3B, which returns peak indexes and intensities as two vectors, DTW(·) is the original dynamic time warping algorithm, cDTW(·) is the constrained dynamic time warping, and ReMapindex(·) is the context-dependent constraint generation discussed with regard to FIGS. 7A to 7D.

To analyze the runtime complexity of the cwDTW algorithm, it is noted that the operations CWT(·), PickPeaks(·) and ReMapindex(·) all have O(N) time- and memory-complexity, where N=max {L1, L2}. Because the cost matrix of cDTW is only filled in the bounded neighborhood of the warping path from the previous level, which grows linearly with a multiplier r, cDTW has O(rN) time- and space-complexity. The number of picked peaks from the CWT spectrum with the $2^{l-1}s_0$ scale is approximately $$\frac{N}{2^l-1}.$$

Thus, in total, $$\sum_{k=0}^{L-1}\frac{N}{2^k} \approx 2N$$

peaks are remapped and considered by the constrained DTW. Therefore, the total runtime of Algorithm 1 is 2·(TIME(cDTW)+TIME(ReMapIndex))+L·TIME(CWT), which gives the time- and memory-complexity of O(2rN+LN), where r,L ≤N. One skilled in the art would understand that the time- and memory-complexity for the cwDTW is smaller than for the existing DTW algorithms, which makes the computing device running the cwDTW method to work more efficient and faster than the existing ones.

Figure 9:
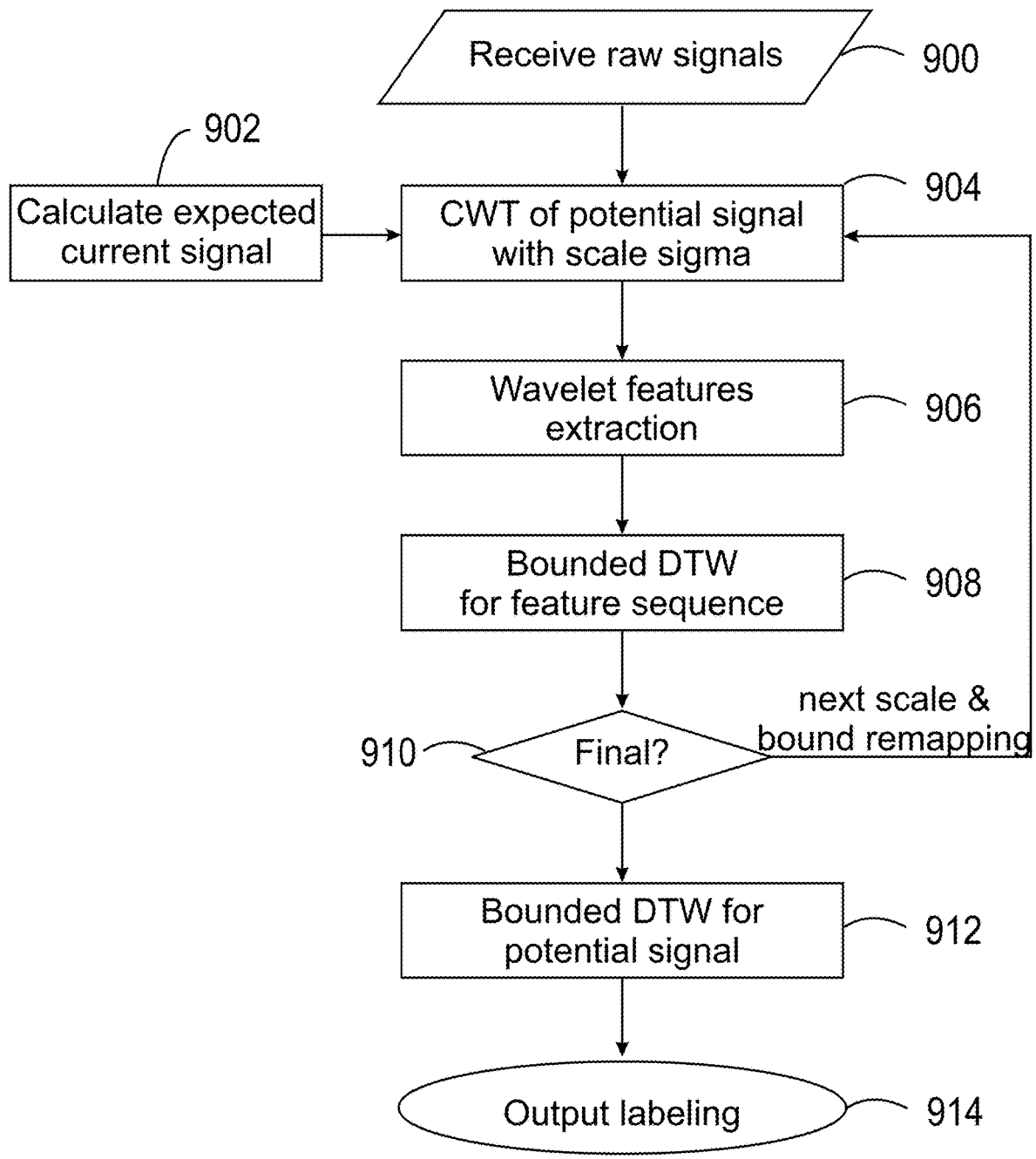
FIG. 9 is a flowchart of a method for identifying a nucleotide sequence.

The cwDTW method discussed above may be summarized as follow with regard to FIG. 9. In step 900, a raw signal 102 is received by the computing device (to be discussed later). As previously discussed, the raw signal $(X_p)$ 102 is an electric signal that is measured with a Nanopore machine (which includes a membrane having a nanopore) when a nucleotide sequence 110 or part of it is passing through the nanopore 112.

In step 902, the pore model is applied to the nucleotide sequence 110 or another nucleotide sequence to calculate the expected current signal $(X_g)$ 130. These two sequences are transformed in step 904 into CWT spectra $X_p^l$ and $X_g^l$, respectively (see also FIG. 5, spectra 322 and 326). This step may include a sub-step of calculating the length ratio $\alpha=|Xp|/|Xg|$ and applying this length ratio to one of the sequences (the longer one).

In step 906, wavelet features 322B and 326B (see FIG. 5) are extracted from the CWT spectra for each sequence. This step may include a sub-step of calculating the CWT spectra for each scale a, normalizing (for example, using the Z-score) the spectra, and then extracting the wavelet features, as illustrated in FIG. 5. In this way, the number of picked features (i.e., peaks and nadirs) from the spectra is substantially identical (within 10% of each other).

Next, in step 908, the extracted features from step 906 are used in a multi-level, bounded, DTW algorithm for calculating the warping path, as illustrated in FIGS. 7A to 7D. If the warping path calculated in step 908 is determined in step 910 to not be the last one, the algorithm returns to step 904, and uses the next scale a. Note that for each iteration, the warping path is calculated with another boundary around a previous warping path, as discussed above. However, if the calculated warping path is the last one, the method advances to step 912 to calculate the potential signal corresponding to the input nucleotide sequence 132 and then outputs in step 914 the nucleotide sequence 132 that corresponds to the potential signal.

The above discussed cwDTW method has been evaluated on two real nanopore datasets, one on human and one on Pandoraea pnomenusa, as well as two benchmark datasets from previous studies [9], which have short sequences with similar lengths.

The first nanopore sequencing dataset is a subset of the public available Human data. This dataset comes from Human chromosome 21 from the Nanopore WGS Consortium [27]. The samples in this dataset were sequenced from the NA12878 human genome reference on the Oxford Nanopore MinION using 1D ligation kits (450 bp/s) with R9.4 flow cells. The nanopore raw signal data in FAST5 format were downloaded from nanopore-wgs-consortium2. The reference genome for Human chromosome 21 was downloaded at NCBI3. The total number of the generated reads in this dataset is 4,530. The average length of the DNA sequences is 7,309, whereas the average length of the nanopore raw signal sequences is 68,628. The temporal scale ratio between the nanopore raw signal and the corresponding DNA sequence is around 9. This dataset is referred to as HM4530.

The second dataset is the genome of one bacterial species named Pandoraea pnomenusa strain 6399. Its reference genome was downloaded from NCBI4. The samples were sequenced on the MinION device with 1D protocol on R9.4 flow cells (FLO-MIN106 protocol). The total number of generated reads is 4,782. The average length of the DNA sequences is 18,590, whereas the average length of the nanopore raw signals is 158,772. Thus, the temporal scale ratio between the nanopore raw signal and the corresponding DNA sequence is around 9. This dataset is referred to as PP4782.

Because both datasets have extremely long sequences, and the raw signal sequences and the expected ones have one order of magnitude difference in length, the experiment mainly compared cwDTW with DTW and FastDTW [9]. DTW is the original method that finds the optimal mapping between the two signal sequences by dynamic programming, whereas FastDTW is the state-of-the-art multi-level DTW method which approximates DTW in linear time- and space-complexity. Other representative DTW algorithms, such as PrunedDTW [11], were designed to measure a similarity between the two sequences. They implicitly assume the lengths of the two sequences to be mapped are comparable and thus cannot handle the unbalanced sequences in the two nanopore datasets.

Therefore, the experiment only included PrunedDTW in a limited comparison over the two benchmark datasets, which have similar lengths for mapped sequences. Both FastDTW and cwDTW have the radius parameter r and the level parameter L, and the cwDTW method has an additional scale parameter $s_0$ to select the base wavelet scale. The performance of the cwDTW method was evaluated with different combinations of $s_0$, r and L. All the methods were run on a Fedora25 system with 128 Gb memory and two E5-2667v4 (3.2 GHz) cores, each with 8 CPUs.

The accuracy of the warping path W generated by an approximate DTW method can be measured by the relative distance difference of W with respect to the optimal path $\hat{W}$ generated by the original DTW [9], as follows:

$$\text{Error}(W) = \frac{Dist(W) - Dist(\hat{W})}{Dist(\hat{W})}. \qquad (2)$$

If an algorithm returns a perfect warping path, the error is zero. Note that the error may exceed 100% if the distance of the warping path is more than twice of that of the optimal path. This embodiment also calculated the normalized deviation of a warping path, nDist(W), by dividing Dist(W) by the length of the warping path.

Figure 10A:
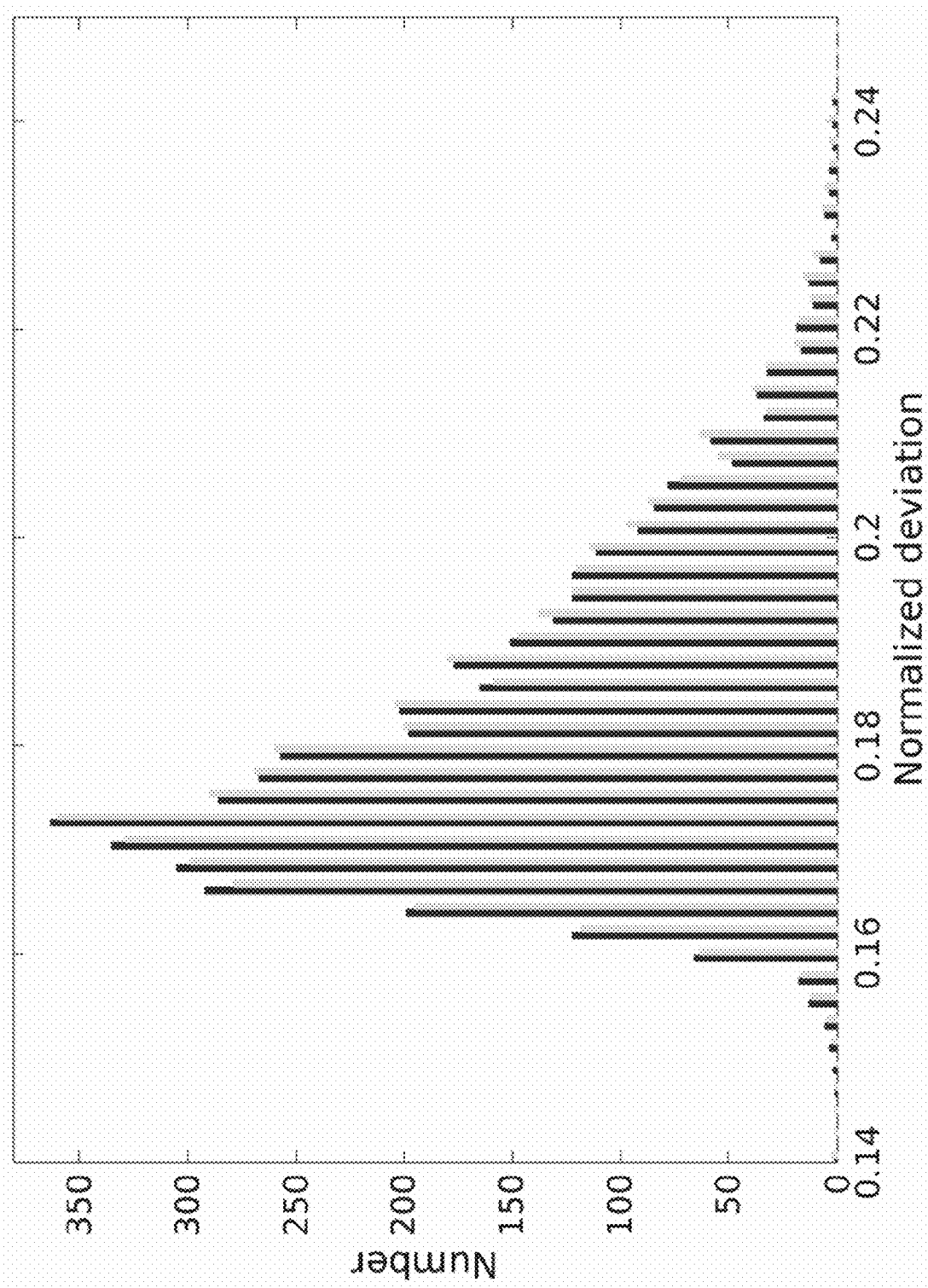
FIGS. 10A and 10B illustrate how the cwDTW algorithm fares comparative with traditional algorithms.
Figure 10B:
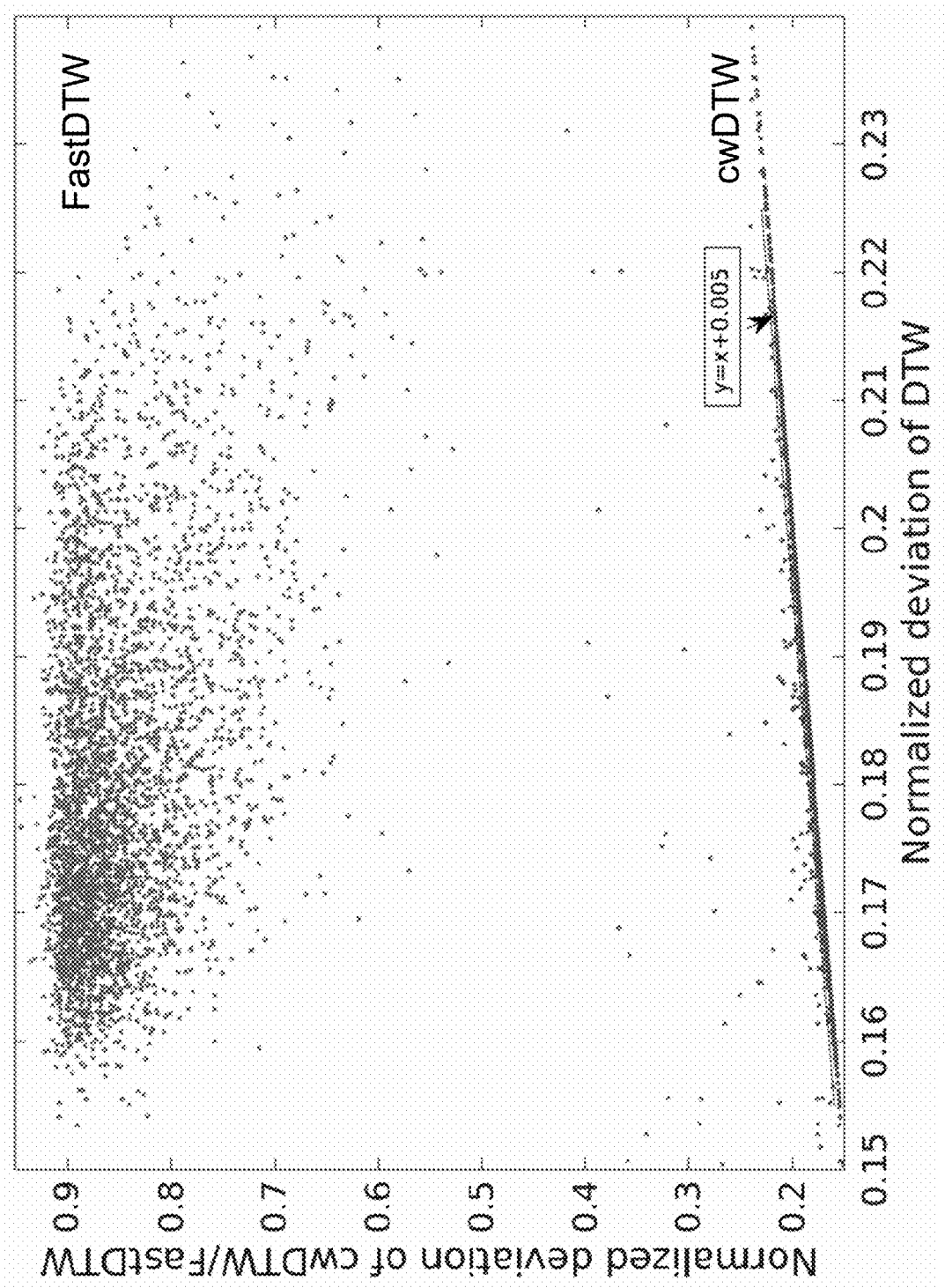

First, the cwDTW method was compared with FastDTW and the original DTW on the HM4530 set. Both the cwDTW and FastDTW have the level set to L=4 and the radius set to r=50, and the base wavelet scale for the cwDTW is set to $s_0=\sqrt{2}$. As shown in FIG. 10A, the distribution of the normalized deviation of cwDTW is very similar to that of the original DTW. FIG. 10B shows the scatter plot between the normalized deviation of the original DTW (x-axis) and that of cwDTW and FastDTW (y-axis). It can be seen from this figure that the mapping accuracy of cwDTW is very close to the original DTW, whereas the FastDTW is far less accurate. In particular, out of the 4,530 reads in the HM4530 set, the cwDTW produces exactly the same optimal warping path as the original DTW on 3,913 reads (86.4%), while on 4,393 reads (97.0%) the normalized deviation of the path generated by cwDTW is within 0.005 margin to that of the optimal path.

In terms of runtime, it took cwDTW 1,406 seconds using a single-CPU (0.31 second on average), whereas FastDTW took 10.7 hours using 16-CPUs in parallel (136 seconds on average) and the original DTW took more than 3 days using 16-CPUs in parallel (916 seconds on average). This indicates that the cwDTW algorithm is about 440 times faster than FastDTW and 3,000 times faster than the original DTW algorithm.

Next, the inventors compared the cwDTW algorithm with the FastDTW algorithm under different radius and scale parameter settings on both HM4530 and PP4782 datasets. As shown in Table 1 in FIG. 11, for different scale parameter values, the mapping error of the cwDTW algorithm is always lower than 1% if the radius is set to at least 50. For the PP4782 set, the cwDTW algorithm can produce the optimal warping path when the scale is small (e.g., 1 or $\sqrt{2}$) and the radius is large (e.g., 90 and 100). On the contrary, the mapping error of the FastDTW algorithm remains higher than 200% on both the HM4530 and PP4782 sets. Enlarging the radius parameter helps reduce the error for the FastDTW algorithm, but the effect is marginal.

The inventors also conducted a detailed parameter sensitivity analysis of the cwDTW method to assess the effects of the three parameters, radius, scale and level, on the average error and runtime. In general, the cwDTW method is quite robust in terms of the average error and runtime with respect to all three parameters. It was found that a high scale parameter (e.g., $s_0=2$) will slightly increase the average error of the cwDTW method on both datasets, while the average error of the cwDTW method almost remains the same for different level parameters. In practice, a radius value of 50 or higher seems to be sufficient. In terms of runtime, different values of the scale parameter do not influence the runtime much, whereas a lower level parameter results in higher runtime. Overall, a higher radius value leads to higher runtime. Summing up these observations, a parameter combination of r=60, $s_0=\sqrt{2}$ and L=4 gives a practically good tradeoff between error and speed for nanopore signal mapping.

One of the advantages of the cwDTW method is the ability to handle signal sequences that have lengths that differ by orders of magnitude. This is achieved by the introduction of the scale factor $\alpha$ in consideration of the length ratio during the CWT process. On the contrary, the FastDTW method performs coarsening by 2-factor downsampling, which does not solve the issue caused by length difference and leads to deviations of the warping path. Such deviations will accumulate through iterations and finally corrupt the results.

To evaluate the performance of the cwDTW method on sequences with similar lengths, two datasets HM4530F and PP4782F were created from HM4530 and PP4782, respectively. The expected signal sequences in HM4530F and PP4782F are the feature sequences extracted by the CWT process with a scale of $\sqrt{2}$ from the expected signal sequences in HM4530 and PP4782, respectively. The raw signal sequences in HM4530F and PP4782F are the feature sequences extracted by the CWT process with scale $8\sqrt{2}$ from the raw signal sequences in HM4530 and PP4782, respectively. Consequently, for HM4530F, the average length of the expected signal sequences is 1,558 and that of the raw signal sequences is 1,572, whereas for PP4782F, the average length of the expected signal sequences is 3,912 and that of the raw signal sequences is 3,957. These two sets thus contain sequences with similar lengths to be mapped.

Table 2 in FIG. 12 summarizes the average error of the FastDTW and cwDTW algorithms with different radius and scale parameter values over the HM4530F and PP4782F datasets. It can be seen that the cwDTW algorithm still drastically outperforms the FastDTW algorithm regardless of the parameter settings. When the radius is at least 60, the cwDTW algorithm can always keep the mapping error to be lower than 1% for both datasets, whereas the error of the FastDTW algorithm is at least 20%. Further experiments show that to reduce the error of the FastDTW algorithm to below 10%, one needs to set the radius parameter to be around 200.

The inventors further tested the cwDTW algorithm on two benchmark datasets, Trace and Gunpoint, used in the evaluation of the FastDTW algorithm [9]. Each of these sets contains sequences with short lengths, ranging from 150 to 275. The comparison results show that the cwDTW algorithm still significantly outperforms both the FastDTW and PrunedDTW algorithm in terms of the average error, under all the settings of the radius parameter. Taking together all the consistent results from Table 1 and Table 2, it can be concluded that the cwDTW algorithm is very robust to the temporal scale, and can handle both balanced and unbalanced cases more efficiently and more accurately than the existing algorithms. Further, the computation improvements discussed above for the cwDTW algorithm is better the Nanopore algorithms.

The inventors further investigated the importance of the feature extraction strategy by peak picking described with regard to FIGS. 4 and 5, for which it was compared the proposed strategy with two alternative approaches: equal averaging and peak averaging. Suppose at level I, there are $L_I$ peaks. The proposed peak picking strategy uses these $L_I$ peaks as the feature sequence. For equal averaging, the original signal sequence is equally partitioned into $L_I$ bins and the average signal values in these bins are extracted as the feature sequence. For peak averaging, the original signal sequence is partitioned according to the locations of the $L_I$ peaks, and the average signal values in the window composed of the left and right half bins of each peak are used as the feature sequence. Therefore, for all three strategies, the length of the feature sequence is the same.

From the comparison between the FastDTW and cwDTW algorithms with three different feature extraction strategies (as discussed in the previous paragraph) over the HM4530F and PP4782F datasets, it is observed that the proposed cwDTW strategy always performs best, regardless of the radius value, followed by the cwDTW method with the peak averaging strategy for feature extraction. This suggests that the peak signals in the CWT approach contains more stable and useful information than the locally averaged values around the peaks.

The performance of the equal averaging strategy, on the other hand, is sensitive to the choice of the scale parameter and is far less than that of the original cwDTW method and the peak averaging strategy. This implies that the peak locations captured by the CWT approach are important to extract useful information. The observed results justify the use of the peak picking strategy as the feature extraction method in the cwDTW algorithm.

The proposed novel continuous wavelet dynamic time warping algorithm for unbalanced global mapping in nanopore sequencing can thus be summarized to perform coarsening on the input signal sequences via CWT with different resolutions. Peaks are picked from CWT sequences to form feature sequences. The warping path obtained from a coarser resolution is used to obtain a context-dependent boundary to constrain the warping path at a refiner resolution. Comprehensive experiments on both real nanopore datasets with unbalanced sequences and benchmark datasets with balanced sequences demonstrated the effectiveness and efficiency of the cwDTW method, which cannot be achieved by the state-of-the-art DTW algorithms. The proposed algorithm provides a powerful tool for various nanopore sequencing tasks, such as base calling, reads mapping, variant identification, and methylation detection. In addition, the generic nature of the cwDTW method makes it a useful method for mapping temporal sequences of biological, video, audio and graphical data.

Figure 13:
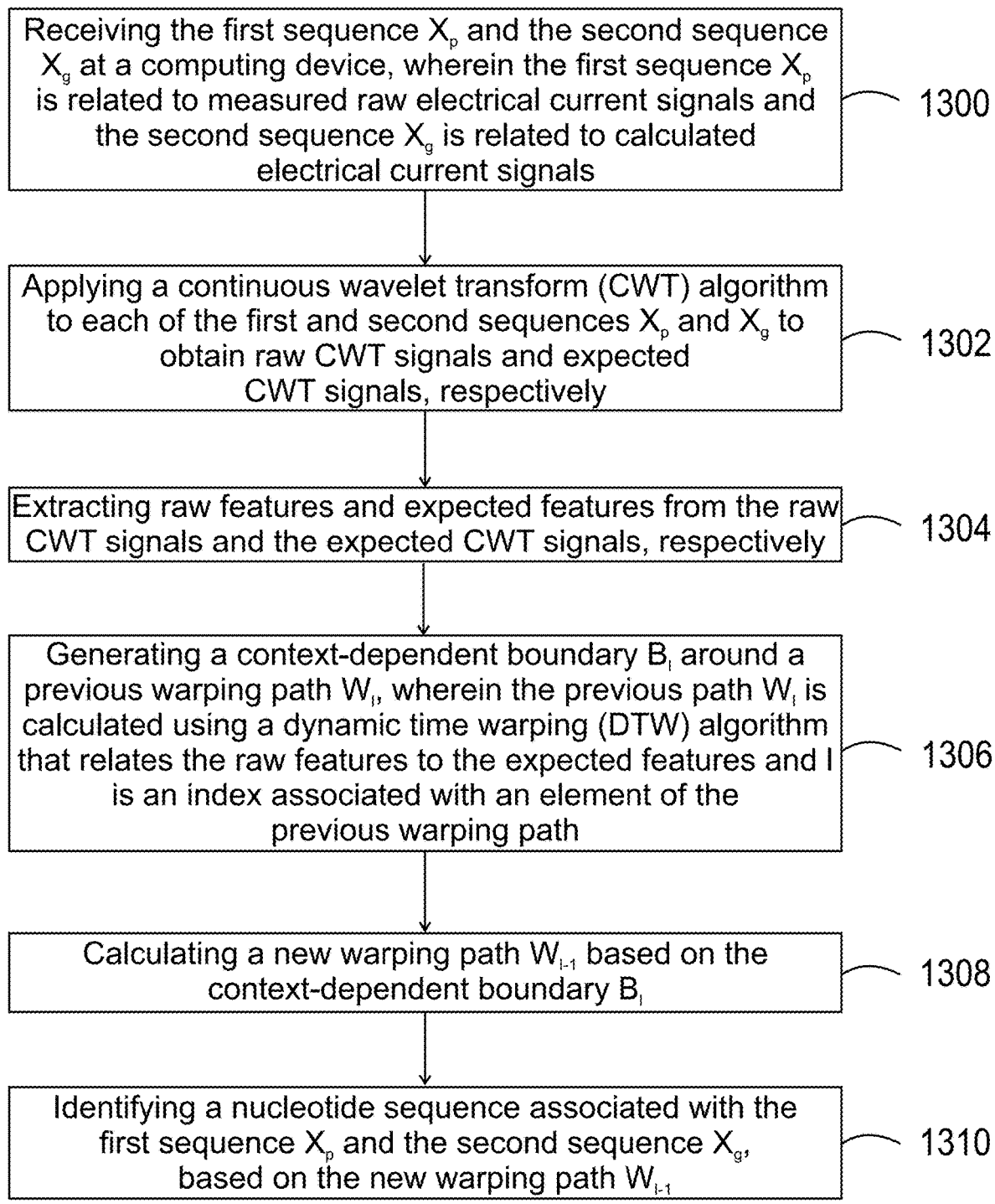
FIG. 13 is a flowchart of a method for identifying a biopolymer using the cwDTW algorithm.

A flowchart of the cwDTW method is illustrated in FIG. 13 and now discussed. The method for global mapping between a first sequence $X_p$ and a second sequence $X_g$ includes a step 1300 of receiving the first sequence Xp and the second sequence Xg at a computing device, wherein the first sequence Xp is related to measured raw electrical current signals and the second sequence Xg is related to calculated electrical current signals; a step 1032 of applying a continuous wavelet transform (CWT) algorithm to each of the first and second sequences Xp and Xg to obtain raw CWT signals and expected CWT signals, respectively; a step 1304 of extracting raw features 322B and expected features 326B from the raw CWT signals 322 and the expected CWT signals 326, respectively; a step 1306 of generating a context-dependent boundary $B_I$ around a previous warping path $W_I$, wherein the previous warping path $W_I$ is calculated using a dynamic time warping (DTW) algorithm that relates the raw features 322B to the expected features 326B and I is an index associated with an element of the previous warping path; a step 1308 of calculating a new warping path $W_{I-1}$ based on the context-dependent boundary $B_I$; and a step 1310 of identifying a nucleotide sequence 132 associated with the first sequence $X_p$ and the second sequence $X_g$, based on the new warping path $W_{I-1}$.

About the step of identifying, the classification of biological sequences (e.g. DNA, RNA, or protein) based on their similarity is a well-known procedure. The similarity between two DNA sequences determined by their evolutionary distance can be used to evaluate the evolutionary relationships of organisms. The evolutionary tree of all living organisms was constructed this way.

The sequence may be a raw electrical current signal sequence and the second sequence may be an expected signal sequence from a pore model. In one application, the step of applying includes obtaining the raw CWT signals and the expected CWT signals at different scales. In another application, the step of extracting includes extracting the peaks of the raw CWT signals 322 and expected CWT signals 326 as the raw features 322B and expected features 326B, respectively.

The method may also include a step of calculating a ratio α of a length of the first and second sequences Xp and Xg; and a step of calculating the raw CWT signals 322 and expected CWT signals 326 as a function of the ratio α. In one variation, the method may include a step of normalizing the raw CWT signals 322 and expected CWT signals 326 based on a Z-score; and a step of calculating the peaks of the normalized signals as the raw features 322B and expected features 326B.

The step of generating may include a step of calculating the context-dependent boundary $B_I$ around a previous warping path $W_I$, for each scale. The context-dependent boundary $B_I$ defines a reduced search space 704 around the previous warping path $W_I$ based on a radius r. In one application, each element in the new warping path of the (I−1)th level in the reduced search space 704 is within the radius r from a corresponding element in the path of the previous Ith level. In still another application, the step of calculating includes applying the DTW algorithm to the raw features 322B and expected features 326B, within only the reduced search space 704, to calculate the new warping path $W_{l-1}$.

Figure 14:
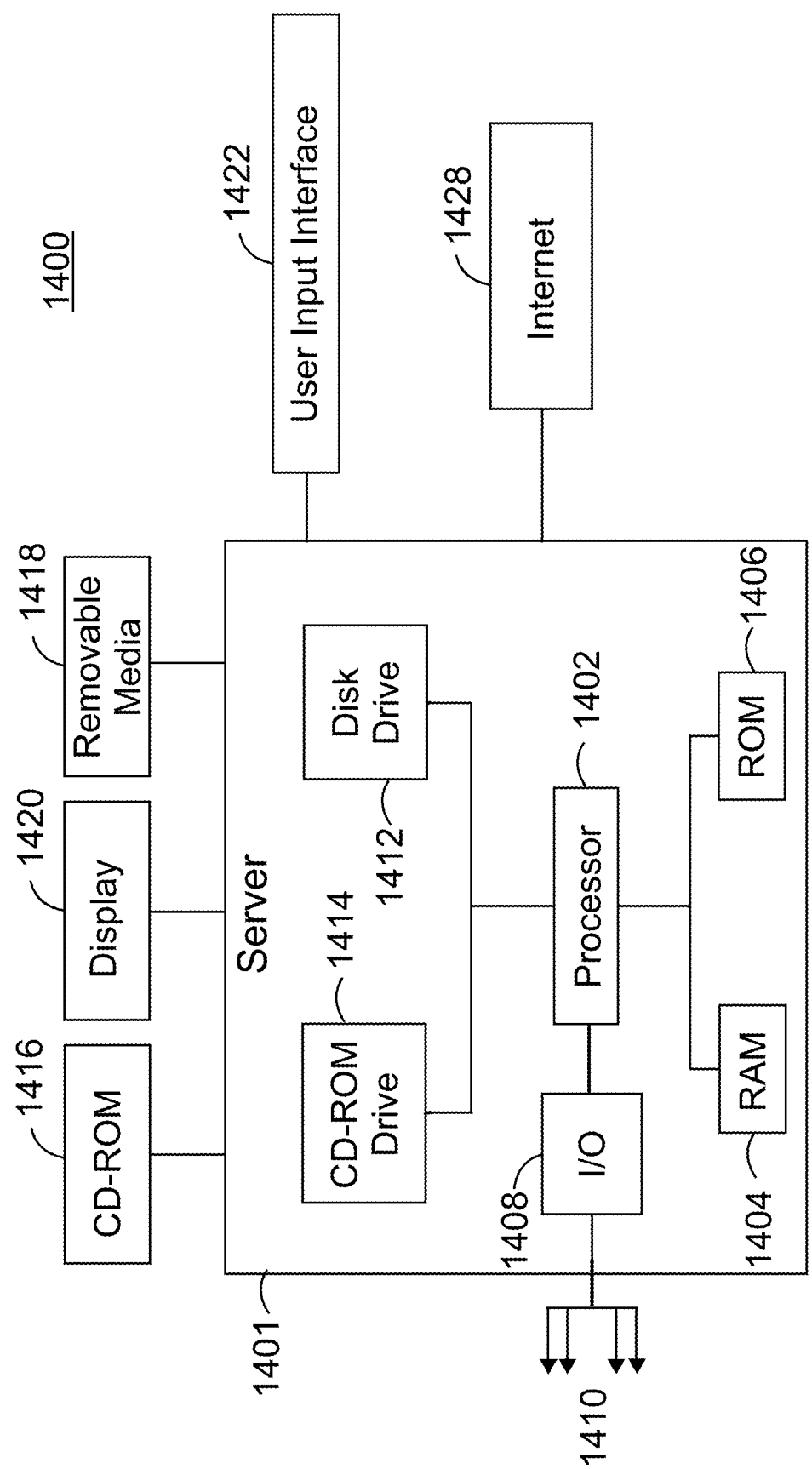
FIG. 14 illustrates a computing device or controller that implements one or more of the methods noted above.

The above-discussed procedures and methods may be implemented in a computing device or controller as illustrated in FIG. 14. Hardware, firmware, software or a combination thereof may be used to perform the various steps and operations described herein. Computing device 1400 of FIG. 14 is an exemplary computing structure that may be used in connection with such a system.

Exemplary computing device 1400 suitable for performing the activities described in the exemplary embodiments may include a server 1401. Such a server 1401 may include a central processor (CPU) 1402 coupled to a random access memory (RAM) 1404 and to a read-only memory (ROM) 1406. ROM 1406 may also be other types of storage media to store programs, such as programmable ROM (PROM), erasable PROM (EPROM), etc. Processor 1402 may communicate with other internal and external components through input/output (I/O) circuitry 1408 and bussing 1410 to provide control signals and the like. Processor 1402 carries out a variety of functions as are known in the art, as dictated by software and/or firmware instructions.

Server 1401 may also include one or more data storage devices, including hard drives 1412, CD-ROM drives 1414 and other hardware capable of reading and/or storing information, such as DVD, etc. In one embodiment, software for carrying out the above-discussed steps may be stored and distributed on a CD-ROM or DVD 1416, a USB storage device 1418 or other form of media capable of portably storing information. These storage media may be inserted into, and read by, devices such as CD-ROM drive 1414, disk drive 1412, etc. Server 1401 may be coupled to a display 1420, which may be any type of known display or presentation screen, such as LCD, plasma display, cathode ray tube (CRT), etc. A user input interface 1422 is provided, including one or more user interface mechanisms such as a mouse, keyboard, microphone, touchpad, touch screen, voice-recognition system, etc.

Server 1401 may be coupled to other devices, such as a smart device, e.g., a phone, tv set, computer, etc. The server may be part of a larger network configuration as in a global area network (GAN) such as the Internet 1428, which allows ultimate connection to various landline and/or mobile computing devices.

The disclosed embodiments provide methods and mechanisms for Nanopore sequencing. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

REFERENCES

[1] M. L. Metzker, "Sequencing technologies—the next generation," Nature reviews. Genetics, vol. 11, no. 1, p. 31, 2010.

[2] M. Jain, I. T. Fiddes, K. H. Miga, H. E. Olsen, B. Paten, and M. Akeson, "Improved data analysis for the minion nanopore sequencer," Nature methods, vol. 12, no. 4, pp. 351-356, 2015.

[3] A. Byrne, A. E. Beaudin, H. E. Olsen, M. Jain, C. Cole, T. Palmer, R. M. DuBois, E. C. Forsberg, M. Akeson, and C. Vollmers, "Nanopore long-read maseq reveals widespread transcriptional variation among the surface receptors of individual b cells," bioRxiv, p. 126847, 2017.

[4] H. Lu, F. Giordano, and Z. Ning, "Oxford nanopore minion sequencing and genome assembly," Genomics, proteomics & bioinformatics, vol. 14, no. 5, pp. 265-279, 2016.

[5] J. T. Simpson, R. E. Workman, P. Zuzarte, M. David, L. Dursi, and W. Timp, "Detecting dna cytosine methylation using nanopore sequencing," nature methods, vol. 14, no. 4, pp. 407-410, 2017.

[6] M. Loose, S. Malla, and M. Stout, "Real-time selective sequencing using nanopore technology," Nature methods, vol. 13, no. 9, pp. 751-754, 2016.

[7] M. David, L. J. Dursi, D. Yao, P. C. Boutros, and J. T. Simpson, "Nanocall: an open source basecaller for oxford nanopore sequencing data," Bioinformatics, p. btw569, 2016.

[8] T. Szalay and J. A. Golovchenko, "De novo sequencing and variant calling with nanopores using poreseq.," Nature biotech-nology, vol. 33, pp. 1087-1091, October 2015.

[9] S. Salvador and P. Chan, "FastDTW: Toward accurate dynamic time warping in linear time and space," Intelligent Data Analysis, vol. 11, no. 5, pp. 561-580, 2007.

[10] G. Al-Naymat, S. Chawla, and J. Taheri, "Sparsedtw: A novel approach to speed up dynamic time warping," in Proceedings of the Eighth Australasian Data Mining Conference-Volume 101, pp. 117-127, Australian Computer Society, Inc., 2009.

[11] D. F. Silva and G. E. A. P. A. Batista, Speeding Up All-Pairwise Dynamic Time Warping Matrix Calculation, pp. 837-845.

[12] C. A. Ratanamahatana and E. Keogh, "Three myths about dynamic time warping data mining," in Proceedings of the 2005 SIAM International Conference on Data Mining, pp. 506-510, SIAM, 2005.

[13] M. Müller, H. Mattes, and F. Kurth, "An efficient multiscale approach to audio synchronization.," in ISMIR, pp. 192-197, 2006.

[14] T. Prätzlich, J. Driedger, and M. Müller, "Memory-restricted multiscale dynamic time warping," in Acoustics, Speech and Signal Processing (ICASSP), 2016 IEEE International Conference on, pp. 569-573, IEEE, 2016.

[15] E. J. Keogh and M. J. Pazzani, "Scaling up dynamic time warping for datamining applications," in Proceedings of the sixth ACM SIGKDD international conference on Knowledge discovery and data mining, pp. 285-289, ACM, 2000.

[16] S. Chu, E. Keogh, D. Hart, and M. Pazzani, "Iterative deepening dynamic time warping for time series," in Proceedings of the 2002 SIAM International Conference on Data Mining, pp. 195-212, SIAM, 2002.

[17] M. Stoiber and J. Brown, "Basecrawller: Streaming nanopore basecalling directly from raw signal," bioRxiv, p. 133058, 2017.

[18] C. Torrence and G. P. Compo, "A practical guide to wavelet analysis," Bulletin of the American Meteorological society, vol. 79, no. 1, pp. 61-78, 1998.

[19] E. Keogh and C. A. Ratanamahatana, "Exact indexing of dynamic time warping," Knowledge and information systems, vol. 7, no. 3, pp. 358-386, 2005.

[20] D. Lemire, "Faster retrieval with a two-pass dynamic-time-warping lower bound," Pattern recognition, vol. 42, no. 9, pp. 2169-2180, 2009.

[21] S. G. Mallat, "A theory for multiresolution signal decomposition: the wavelet representation," IEEE transactions on pattern analysis and machine intelligence, vol. 11, no. 7, pp. 674-693, 1989.

[22] J. Z. Song, K. M. Duan, T. Ware, and M. Surette, "The wavelet-based cluster analysis for temporal gene expression data," EURASIP Journal on Bioinformatics and Systems Biology, vol. 2007, pp. 2-2, 2007.

What is claimed is:

1. A method for global mapping between a first sequence $X_p$ and a second sequence $X_g$, the method comprising:
receiving the first sequence $X_p$ and the second sequence $X_g$ at a computing device, wherein the first sequence $X_p$ is related to a nucleotide sequence of a cell, and includes raw electrical current signals measured as the nucleotide sequence passes through a pore in a membrane of a nanopore machine, and the second sequence $X_g$ is related to electrical current signals calculated based on a pore model of the nucleotide sequence;
applying a continuous wavelet transform (CWT) algorithm to each of the first and second sequences $X_p$ and $X_g$ to obtain raw CWT signals and expected CWT signals, respectively;
extracting raw features and expected features from the raw CWT signals and the expected CWT signals, respectively;
generating a context-dependent boundary Bi around a previous warping path $W_I$, wherein the previous warping path $W_I$ is calculated using a dynamic time warping (DTW) algorithm that relates the raw features to the expected features and I is an index associated with an element of the previous warping path;
calculating a new warping path $W_{I-1}$ based on the context-dependent boundary $B_I$; and
identifying the nucleotide sequence associated with the first sequence $X_p$ and the second sequence $X_g$, based on the new warping path $W_{I-1}$.

2. The method of claim 1, wherein the first sequence is a raw electrical current signal sequence and the second sequence is an expected signal sequence from pore model.

3. The method of claim 1, wherein the step of applying comprises:
obtaining the raw CWT signals and the expected CWT signals at different scales.

4. The method of claim 3, wherein the step of extracting comprises:
extracting the peaks of the raw CWT signals and expected CWT signals as the raw features and expected features, respectively.

5. The method of claim 4, further comprising:
calculating a ratio α of a length of the first and second sequences $X_p$ and $X_g$; and
calculating the raw CWT signals and expected CWT signals as a function of the ratio α.

6. The method of claim 5, further comprising:
normalizing the raw CWT signals and expected CWT signals based on a Z-score; and
calculating the peaks of the normalized signals as the raw features and expected features.

7. The method of claim 3, wherein the step of generating comprises:
calculating the context-dependent boundary Bi around a previous warping path $W_I$, for each scale.

8. The method of claim 7, wherein the context-dependent boundary $B_I$ defines a reduced search space around the previous warping path $W_I$ based on a radius r.

9. The method of claim 8, wherein each element in the new warping path at a (I-1)th level in the reduced search space is within the radius r from a corresponding element in the path of the previous Ith level.

10. The method of claim 9, wherein the step of calculating comprises:
applying the DTW algorithm to the raw features and expected features, within only the reduced search space, to calculate the new warping path $W_{I-1}$.

11. A computing device for global mapping between a first sequence $X_p$ and a second sequence $X_g$, the computing device comprising:
an interface configured to receive the first sequence $X_p$ and the second sequence $X_g$, wherein the first sequence $X_p$ is related to a nucleotide sequence of a cell, and includes raw electrical current signals measured as the nucleotide sequence passes through a pore in a membrane of a nanopore machine, and the second sequence $X_g$ is related to electrical current signals calculated based on a pore model of the nucleotide sequence; and
a processor connected to the interface, the processor being configured to,
apply a continuous wavelet transform (CWT) algorithm to each of the first and second sequences $X_p$ and $X_g$ to obtain raw CWT signals and expected CWT signals, respectively,
extract raw features and expected features from the raw CWT signals and the expected CWT signals, respectively,
generate a context-dependent boundary $B_I$ around a previous warping path $W_I$, wherein the previous warping path WI is calculated using a dynamic time warping (DTW) algorithm that relates the raw features to the expected features and I is an index associated with an element of the previous warping path,
calculate a new warping path $W_{I-1}$ based on the context-dependent boundary $B_I$, and
identify the nucleotide sequence associated with the first sequence $X_p$ and the second sequence $X_g$, based on the new warping path $W_{I-1}$.

12. The device of claim 11, wherein the first sequence is a raw electrical current signal sequence and the second sequence is an expected signal sequence from the pore model.

13. The device of claim 11, wherein the processor is further configured to:
obtain the raw CWT signals and the expected CWT signals at different scales.

14. The device of claim 13, wherein the processor is further configured to:
extract the peaks of the raw CWT signals and expected CWT signals as the raw features and expected features, respectively.

15. The device of claim 14, wherein the processor is further configured to:
calculate a ratio $\alpha$ of a length of the first and second sequences $X_p$ and $X_g$; and
calculate the raw CWT signals and expected CWT signals as a function of the ratio $\alpha$.

16. The device of claim 15, wherein the processor is further configured to:
normalize the raw CWT signals and expected CWT signals based on a Z-score; and
calculate the peaks of the normalized signals as the raw features and expected features.

17. The device of claim 13, wherein the processor is further configured to:
calculate the context-dependent boundary Bi around a previous warping path $W_I$, for each scale.

18. The device of claim 17, wherein the context-dependent boundary $B_I$ defines a reduced search space around the previous warping path $W_I$ based on a radius r.

19. The device of claim 18, wherein each element in the new warping path at a (I-1)th level in the reduced search space is within the radius r from a corresponding element in the path of the previous Ith level.

20. A non-transitory computer readable medium including computer executable instructions, wherein the instructions, when executed by a processor, implement instructions for executing global mapping between a first sequence $X_p$ and a second sequence $X_g$, the instructions comprising:
receiving the first sequence $X_p$ and the second sequence $X_g$ at a computing device, wherein the first sequence $X_p$ is related to a nucleotide sequence of a cell, and includes raw electrical current signals measured as the nucleotide sequence passes through a pore in a membrane of a nanopore machine, and the second sequence $X_g$ is related to electrical current signals calculated based on a pore model of the nucleotide sequence;
applying a continuous wavelet transform (CWT) algorithm to each of the first and second sequences $X_p$ and $X_g$ to obtain raw CWT signals and expected CWT signals, respectively;
extracting raw features and expected features from the raw CWT signals and the expected CWT signals, respectively;
generating a context-dependent boundary $B_I$ around a previous warping path $W_I$, wherein the previous warping path WI is calculated using a dynamic time warping (DTW) algorithm that relates the raw features to the expected features and I is an index associated with an element of the previous warping path;
calculating a new warping path $W_{I-1}$ based on the context-dependent boundary $B_I$; and
identifying the nucleotide sequence associated with the first sequence $X_p$ and the second sequence $X_g$, based on the new warping path $W_{I-1}$.

* * * * *